US009743685B2

(12) United States Patent
Lages et al.

(10) Patent No.: US 9,743,685 B2
(45) Date of Patent: Aug. 29, 2017

(54) MIXTURES HAVING IMPROVED COOLING EFFECT

(71) Applicant: SYMRISE AG, Holzminden (DE)

(72) Inventors: Rita Lages, Bodenwerder (DE); Hubert Loges, Hoexter (DE); Arnold Machinek, Holzminden (DE); Gabriele Neuendorff, Holzminden (DE); Erich Dilk, Holzminden (DE); Heiko Oertling, Lausanne (CH)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 14/401,691

(22) PCT Filed: Apr. 18, 2013

(86) PCT No.: PCT/EP2013/058118
§ 371 (c)(1),
(2) Date: Nov. 17, 2014

(87) PCT Pub. No.: WO2013/171018
PCT Pub. Date: Nov. 21, 2013

(65) Prior Publication Data
US 2015/0139918 A1 May 21, 2015

(30) Foreign Application Priority Data
May 16, 2012 (EP) .................................... 12003859

(51) Int. Cl.
A23L 1/22 (2006.01)
A23L 1/226 (2006.01)
A61K 8/33 (2006.01)
A61K 8/34 (2006.01)
A61K 31/11 (2006.01)
A61K 31/045 (2006.01)
A61Q 11/00 (2006.01)
A23G 4/06 (2006.01)
A23G 3/36 (2006.01)
A23G 3/38 (2006.01)
A61Q 19/00 (2006.01)
A23G 9/32 (2006.01)
A23L 27/00 (2016.01)
A23L 27/20 (2016.01)

(52) U.S. Cl.
CPC ............ *A23L 1/22091* (2013.01); *A23G 3/36* (2013.01); *A23G 3/38* (2013.01); *A23G 4/06* (2013.01); *A23G 9/32* (2013.01); *A23L 27/204* (2016.08); *A23L 27/86* (2016.08); *A23L 27/88* (2016.08); *A61K 8/33* (2013.01); *A61K 8/34* (2013.01); *A61K 31/045* (2013.01); *A61K 31/11* (2013.01); *A61Q 11/00* (2013.01); *A61Q 19/00* (2013.01); *A23V 2002/00* (2013.01); *A61K 2800/244* (2013.01)

(58) Field of Classification Search
None
See application file for complete search history.

(56) References Cited

U.S. PATENT DOCUMENTS

| | | | |
|---|---|---|---|
| 3,111,127 A | 11/1963 | Jarboe | |
| 3,419,543 A | 12/1968 | Mold et al. | |
| 3,488,419 A | 1/1970 | McCune et al. | |
| 3,879,425 A | 4/1975 | Hall et al. | |
| 3,922,237 A * | 11/1975 | Schreiber | A23L 1/22657 424/76.4 |
| 4,157,384 A | 6/1979 | Watson et al. | |
| 4,198,393 A * | 4/1980 | Yoshida | A23G 4/06 424/49 |
| 4,459,425 A | 7/1984 | Amano et al. | |
| 5,286,500 A | 2/1994 | Synosky et al. | |
| 5,585,343 A * | 12/1996 | McGee | A61Q 13/00 512/1 |
| 5,703,123 A | 12/1997 | Pelzer et al. | |
| 5,725,865 A | 3/1998 | Mane et al. | |
| 5,843,466 A | 12/1998 | Mane et al. | |
| 5,945,088 A * | 8/1999 | Delli Santi | A61K 8/34 424/49 |
| 6,328,982 B1 | 12/2001 | Shiroyama et al. | |
| 6,407,293 B1 | 6/2002 | Amano et al. | |
| 6,515,188 B2 | 2/2003 | Amano et al. | |

(Continued)

FOREIGN PATENT DOCUMENTS

| | | |
|---|---|---|
| DE | 1921560 | 11/1969 |
| DE | 2224430 | 12/1973 |
| DE | 2343196 | 4/1975 |

(Continued)

OTHER PUBLICATIONS

Shrivastava Alankar. A Review on Peppermint Oil. Asian Journal of Pharmaceutical and Clinical Research. vol. 2, Issue 2, Apr.-Jun. 2009, pp. 27-33.*
Yoshitaka Ueyama, Seiji Hashimoto, Hiromichi Nii, and Kiyoshi Furukawa. The Essential Oil from the Flowers of *Campsis grandiflora* (Thumb.) K. Schum. from China. Flavour and Fragrance Journal, vol. 4, 103-107 (1989).*
Watson et al. J. Soc. Cosmet. Chem. 1978, vol. 29, p. 185-200, "New compounds with the menthol cooling effect."
Maruoka et al. J. Am. Chem. Soc. 1988, vol. 110, p. 7922-7924, "Unprecedented Stereochemical Control in the Claisen Rearrangement of Allyl Vinyl Ethers Using Organoaluminum Reagents."

(Continued)

*Primary Examiner* — Frederick Krass
*Assistant Examiner* — Michael P Cohen
(74) *Attorney, Agent, or Firm* — Brooks Kushman P.C.

(57) ABSTRACT

A mixtures which contain (a) at least one phenylalkenal of formula (I) wherein $R_1$ and $R_2$ independently represent hydrogen, a methyl or phenyl group, $R_3$ represents hydrogen, a phenyl group, alkenyl group or a linear or branched alkyl group with 1 to 5 carbon atoms, and the broken double lines independently represent a single bond or a double bond, and (b) at least one physiological cooling agent.

20 Claims, No Drawings

(56) References Cited

U.S. PATENT DOCUMENTS

| | | | |
|---|---|---|---|
| 2011/0195042 A1 | 8/2011 | Huetter et al. | |
| 2012/0201778 A1* | 8/2012 | Casazza | A61L 9/01 424/76.1 |

FOREIGN PATENT DOCUMENTS

| | | | |
|---|---|---|---|
| DE | 2608226 | 9/1977 | |
| DE | 4226043 | 2/1994 | |
| EP | 0988852 | 3/2000 | |
| EP | 1332772 | 8/2003 | |
| FR | WO 2010146258 A2 * | 12/2010 | A61K 8/35 |
| JP | 2004135522 | 5/2004 | |
| JP | 2006020526 | 1/2006 | |
| JP | 2006025706 | 2/2006 | |
| JP | 2006121958 | 5/2006 | |
| WO | 0001321 | 1/2000 | |
| WO | 0062737 | 10/2000 | |
| WO | 02091849 | 11/2002 | |
| WO | 03043431 | 5/2003 | |
| WO | 2008011742 | 1/2008 | |
| WO | 2008049581 | 5/2008 | |
| WO | 2008107137 | 9/2008 | |
| WO | 2008149102 | 12/2008 | |
| WO | 2010146258 | 12/2010 | |

OTHER PUBLICATIONS

Lochhead et al. Cosmetics and Toiletries May 1993, vol. 108, 37 Pages, "Encyclopedia of Polymers and Thickeners for Cosmetics."
International Search Report for PCT/EP2013/058118, English translation attached to original, Both completed by the European Patent Office on Jan. 28, 2014, All together 9 pages.

* cited by examiner

MIXTURES HAVING IMPROVED COOLING EFFECT

CROSS-REFERENCE TO RELATED APPLICATION

This application is the U.S. national phase of PCT Application No. PCT/EP2013/058118 filed on Apr. 18, 2013, which claims priority to EP Patent Application No. 12003859.1 filed on May 16, 2012, the disclosures of which are incorporated in their entirety by reference herein.

FIELD OF THE INVENTION

The invention is within the area of substances that have a cooling sensory effect and relates to mixtures having an improved cooling effect and to preparations that contain these mixtures.

PRIOR ART

In order to meet consumers' demands for new odor and taste experiences, in the aroma and flavors industry there is a considerable demand for substances that possess excellent sensory (i.e. perceptible with the senses) properties and with which notable novel effects can be achieved. Apart from the pure odor and taste properties, other additional properties may be important, for example such that the odor and taste sensations are inhibited or intensified.

Aroma or flavor compositions with a cooling effect impart, e.g. to mouth hygiene products, such as toothpastes and mouthwashes, and confectionery such as candy and chewing gums, their typical, fresh taste that is perceived as pleasant.

Substances that are used on a large scale for the production of these aroma or flavor compositions having a cooling effect are for example eucalyptol (1,8-cineol) and menthol. However, the use of these substances has some disadvantages. Thus, in addition to its cooling effect, eucalyptol has a very strong characteristic medical taste, which is perceived as repulsive by many consumers, especially when eucalyptol is used in higher dosages. When menthol is used, there is a certain delay in the cooling effect, and at higher dosages menthol develops a characteristic bitter, sharp and pungent taste, which has a rather unpleasant effect.

The problem to be solved by the present invention was therefore to provide formulations that have an improved physiological cooling effect and yet have slight or reduced undesirable properties, i.e. additionally also improve the gustatory perception of the cooling agents.

DESCRIPTION OF THE INVENTION

The invention relates to mixtures containing
(a) at least one phenylalkenal of formula (I)

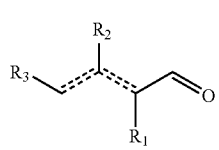

(I)

in which $R_1$ and $R_2$ independently of one another represent hydrogen, a methyl or phenyl residue, $R_3$ stands for hydrogen, a phenyl, an alkenyl or a linear or branched alkyl residue with 1 to 5 carbon atoms, and the broken double lines represent, independently of one another, a single bond or a double bond, and
(b) at least one physiological cooling agent.

It was found, surprisingly, that the mixture according to the invention has an intensified cooling effect, without intensifying the undesirable properties of the physiological cooling agents, such as stinging, burning or bitterness. In particular, on intensifying the cooling effect of the physiological cooling agents, even a reduction of stinging, burning or bitterness may be achieved.

This effect could not be foreseen, since it is described in the prior art that 2-phenyl-but-2-enal is used according to DE1921560 precisely to give foodstuffs a pungent cocoa note. It is also surprising that the mixtures according to the invention do not have cocoa, nut, coffee or fish notes.

Phenylalkenals

Phenylalkenals (component a) are known substances, which are obtainable by the relevant methods of organic chemistry and are described for example by Maruoka et al. in JACS 11, p. 7922-7924 (1988).

2-Phenyl-but-2-enal already finds application in a great variety of compositions. Thus, the use of 2-phenyl-but-2-enal in deodorant compositions is described in WO 2010 146258 A and its use as preservative is described in WO 2008 149102 A. In WO 2008 049581 A, 2-phenyl-but-2-enal is disclosed in milk flavors and in WO 2008 011742 A it is disclosed as taste precursors for foodstuffs. JP 2006 121958 A, JP 2006 025706 A, JP 200 620526 A, JP 2004 135522 A and DE 1921560 A disclose 2-phenyl-but-2-enal for improving cocoa, nut, coffee and fish flavors.

Phenylalkenals of formula (I) in which $R_1$ and $R_2$ are different and denote hydrogen or phenyl, $R_3$ stands for hydrogen, an alkenyl or a linear or branched alkyl group with 1 to 5 carbon atoms, and the broken double lines represent, independently of one another, a single bond or a double bond, are especially preferred in the sense of the invention.

In a quite especially preferred embodiment of the invention, the phenylalkenal according to formula (I) is selected from the group comprising 2-phenyl-but-2-enal, 2-phenyl-pent-2-enal, 3-phenyl-pent-4-enal, 2-phenyl-pent-4-enal and mixtures thereof.

The formulas and CAS numbers of the especially preferred compounds are given in the following Table I:

TABLE I

CAS numbers and formulas of the preferred embodiments for component a

| Name | CAS No. | Formula |
|---|---|---|
| 2-Phenyl-but-2-enal | 4411-89-6 | |

Formula Ia

TABLE I-continued

CAS numbers and formulas of the preferred embodiments for component a

| Name | CAS No. | Formula |
|---|---|---|
| 2-Phenyl-pent-2-enal | 3491-63-2 | Formula Ib |
| 3-Phenyl-pent-4-enal | 939-21-9 | Formula Ic |
| 2-Phenyl-pent-4-enal | CAS 24401-36-3 | Formula Id |

Cooling Agents

Physiological cooling agents (component b) that are suitable in the sense of the present invention are predominantly menthol or menthol compounds. Physiological means in this context that they are also permitted for oral use.

These comprise—along with the main substance menthol itself—menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyl oxamate, monomethyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849) and the menthane-carboxylic acid esters and amides WS-3, WS-4, WS-5, WS-12, WS-14 and WS-30 and mixtures thereof.

[1] FEMA stands for "Flavor and Extracts Manufacturers Association" and GRAS is defined as "Generally Regarded As Safe". A FEMA GRAS designation means that the substance thus characterized has been tested by standard methods and is considered to be toxicologically harmless.

A first important representative of the substances that form component (b) is monomenthyl succinate (FEMA GRAS 3810), which was patented as a substance way back in 1963 by Brown & Williamson Tobacco Corp. (U.S. Pat. No. 3,111,127) and, as a cooling agent, is the object of patent rights U.S. Pat. Nos. 5,725,865 and 5,843,466 (V.Mane Fils). Both the succinate and the analogous monomenthyl glutarate (FEMA GRAS 4006) are important representatives of monomenthyl esters based on di- and polycarboxylic acids:

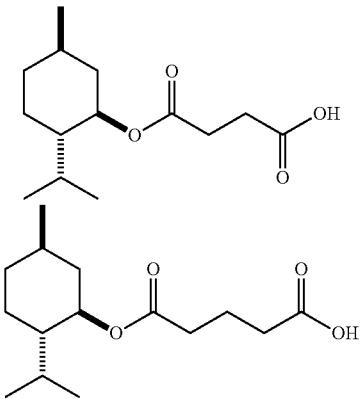

Examples of applications of these substances are to be found for example in documents WO 2003 043431 (Unilever) or EP 1332772 A1 (IFF).

The next important group of menthol compounds that are preferred in the sense of the invention comprises carbonate esters of menthol and polyols, for example glycols, glycerol or carbohydrates, such as for example menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives:

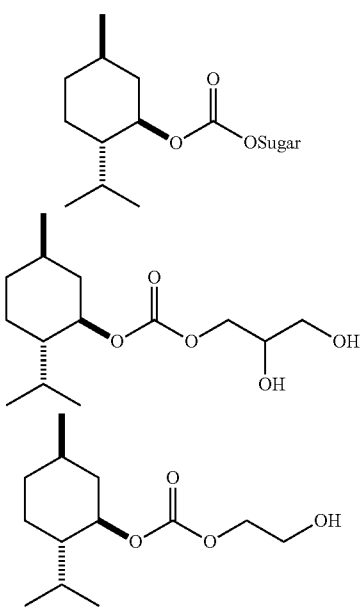

Menthol ethylene glycol carbonate

The use of such substances as cooling agent for cigarettes is for example the object of document U.S. Pat. No. 3,419,543 (Mold et al.) from the year 1968; the use as physiological cooling agent is claimed in DE 4226043 A1 (H&R).

The menthol compounds menthyl lactate (FEMA GRAS 3748=Frescolat® ML) and especially menthone glyceryl acetal (FEMA GRAS 3807) or menthone glyceryl ketal (FEMA GRAS 3808), which is marketed under the designation Frescolat® MGA, are preferred in the sense of the invention.

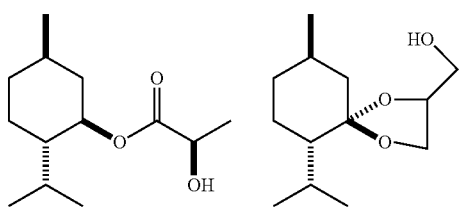

The first structure is obtained by esterification of lactic acid with menthol, and the second one by acetalization of menthone with glycerol (cf. DE 2608226 A1, H&R). This group of compounds also includes 3-(L-menthoxy)propane-1,2-diol, which is also known as Cooling Agent 10 (FEMA GRAS 3784, cf. U.S. Pat. No. 6,328,982, TIC), and 3-(L-menthoxy)-2-methyl-1,2-propanediol (FEMA GRAS 3849), which has an additional methyl group.

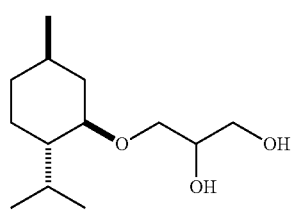

Cooling Agent 10

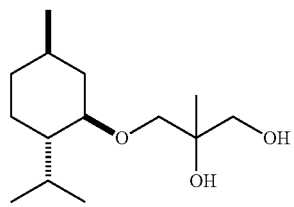

l-Menthoxy-2-methyl 1.2-propanediol 3-(L-Menthoxy)propane-1,2-diol is produced for example starting from menthol according to the following scheme (cf. U.S. Pat. No. 4,459,425, Takagaso):

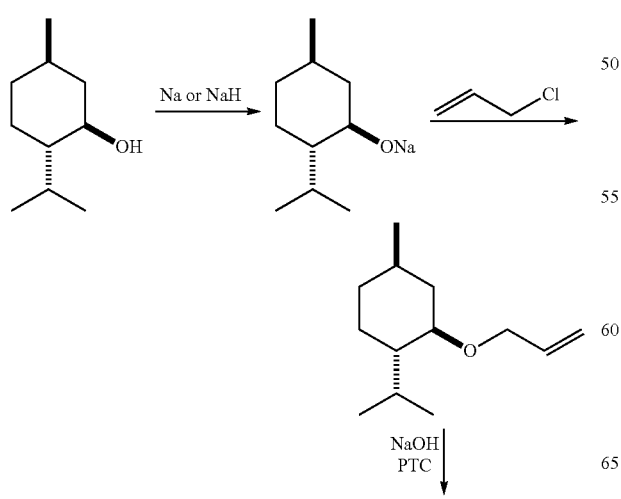

Alternative routes, in which menthol is reacted with epichlorohydrin in the first step, are described in U.S. Pat. Nos. 6,407,293 and 6,515,188 (Takagaso). A review of the preferred menthol compounds that are characterized by a CO bond is given below:

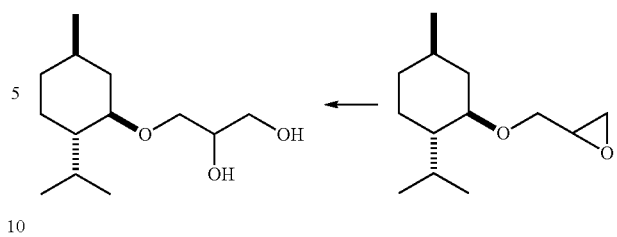

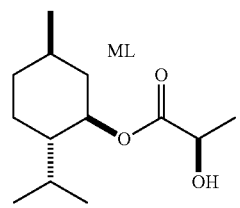

3748
ML

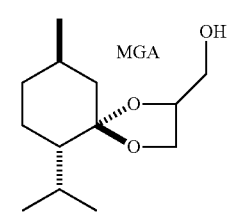

3807
MGA

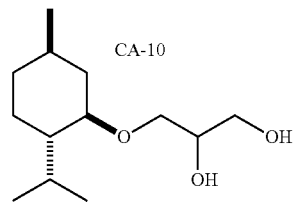

3784
CA-10

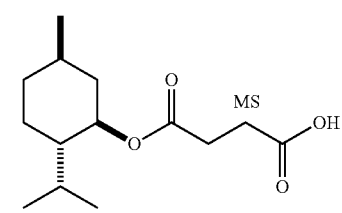

3810
MS

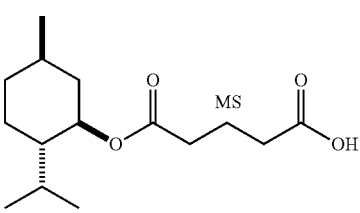

4006
MS

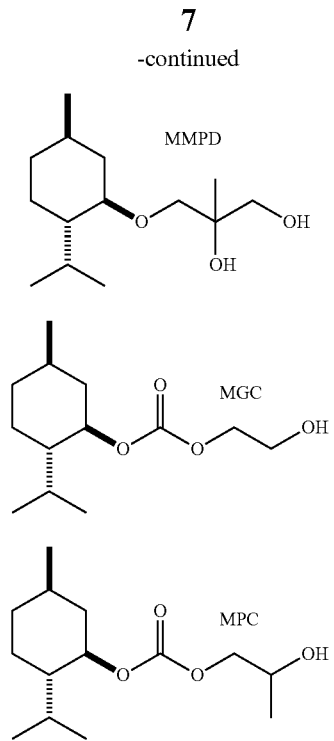

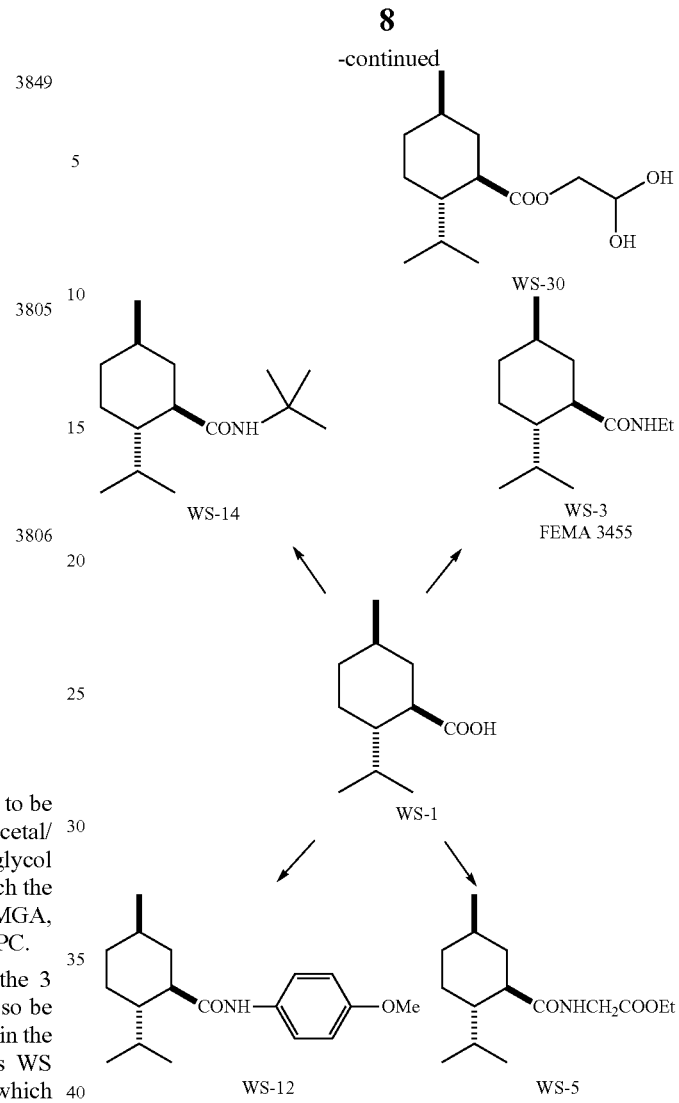

Among these substances, the following have proved to be quite especially advantageous: menthone glyceryl acetal/ketal and menthyl lactate and menthol ethylene glycol carbonate or menthol propylene glycol carbonate, which the applicant sells under the designations Frescolat® MGA, Frescolat® ML, Frescolat® MGC and Frescolat® MPC.

Menthol compounds that have a C—C bond in the 3 position, a number of representatives of which may also be used in the sense of the invention, were first developed in the 1970s. These substances are generally designated as WS types. The main substance is a menthol derivative, in which the hydroxyl group is replaced with a carboxyl group (WS-1). All the other WS types are derived from this structure, for example the species WS-3, WS-4, WS-5, WS-12, WS-14 and WS-30, which are also preferred in the sense of the invention. The following two diagrams show the synthesis routes:

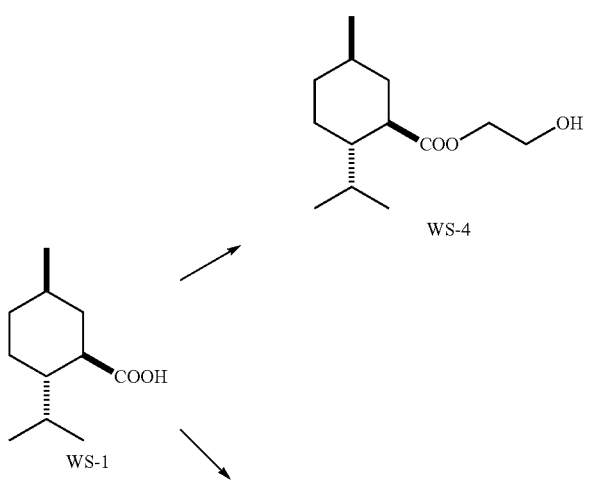

The esters that are derived from WS-1 are described for example in U.S. Pat. No. 4,157,384, and the corresponding N-substituted amides are described in J. Soc. Cosmet. Chem. p. 185-200 (1978).

Especially preferred preparations are those that contain, as component (b), cooling agents that are selected from the group comprising menthol, L-menthol, menthone glycerol acetal, menthyl lactate, substituted menthane-3-carboxylic acid amides, menthane-3-carboxylic acid-N-ethylamide, 2-isopropyl-N,2,3-trimethylbutanamide, substituted cyclohexane-carboxylic acid amides, 3-menthoxy-1,2-propanediol, 2-hydroxyethylmenthyl carbonate, 2-hydroxypropylmenthyl carbonate, N-acetylglycine menthyl esters, menthylhydroxy-carboxylic acid esters, menthyl-3-hydroxybutyrate, menthyl monosuccinate, 2-mercaptocyclodecanone, menthyl-2-pyrrolidin-5-one carboxylate and mixtures thereof.

Other Additives

In a preferred embodiment of the present invention, the mixtures may further contain as optional components (c) at least one aroma substance and/or
(d) at least one solvent.

1. Aroma Substances

The mixtures according to the invention may contain, as optional component (c), one or more aroma substances.

Typical examples comprise: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineol, cinnamyl acetate, citral, citronellol, citronellal, citronellyl acetate, cyclohexyl acetate, cymol, damascone, decalactone, dihydrocoumarin, dimethyl anthranilate, dimethyl anthranilate, dodecalactone, ethoxyethyl acetate, ethyl butyric acid, ethyl butyrate, ethyl caprate, ethyl caproate, ethyl crotonate, ethyl furaneol, ethyl guaiacol, ethyl isobutyrate, ethyl isovalerate, ethyl lactate, ethyl methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyldihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropylmethylthiazole, lauric acid, levulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methylcyclopentenolone, 6,5,2-methylheptenone, methyl dihydrojasmonate, methyl jasmonate, 2-methylmethyl butyrate, 2-methyl-2-pentenolic acid, methyl-thiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethyl vanillin, ethyl vanillin isobutyrate (=3-ethoxy-4-isobutyryloxybenzaldehyde), 2,5-dimethyl-4-hydroxy-3(2H)-furanone and derivatives thereof (and preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (and preferably ethyl maltol), coumarin and coumarin derivatives, gamma-lactones (and preferably gamma-undecalactone, gamma-nonalactone, gamma-decalactone), delta-lactones (and preferably 4-methyldeltadecalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, acetic acid isoamyl esters, butyric acid ethyl esters, butyric acid-n-butyl esters, butyric acid isoamyl esters, 3-methyl-butyric acid ethyl esters, n-hexanoic acid ethyl esters, n-hexanoic acid allyl esters, n-hexanoic acid-n-butyl esters, n-octanoic acid ethyl esters, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2 (5H)-furanone, cinnamaldehyde, cinnamyl alcohol, methylsalicylate, isopulegol and (not explicitly stated here) stereoisomers, enantiomers, positional isomers, diastereomers, cis/trans isomers or epimers of these substances.

Preferably, however, the aromas are selected from the group comprising anethole, menthone, isomenthone, menthyl acetate, menthofuran, mint lactone, eucalyptol, limonene, eugenol, pinene, sabinene hydrate, 3-octanol, carvone, gamma-octalactone, gamma-nonalactone, germacrene D, viridiflorol, 1,3E,5Z-undecatriene, isopulegol, piperitone, 2-butanone, ethyl formate, 3-octyl acetate, isoamyl isovalerate, hexanol, hexanal, cis-3-hexenol, linalool, alpha-terpineol, cis and trans carvyl acetate, p-cymene, damascenone, damascone, rose oxide, dimethylsulfide, fenchol, acetaldehyde diethylacetal, cis-4-heptenal, isobutyraldehyde, isovaleraldehyde, cis-jasmone, anisaldehyde, methylsalicylate, myrtenyl acetate, 2-phenylethyl alcohol, 2-phenylethylisobutyrate, 2-phenylethylisovalerate, cinnamaldehyde, geraniol, nerol and mixtures thereof.

2. Solvents

Furthermore, the mixtures may contain solvents as optional component (d). In particular, those may come into consideration that are selected from the group comprising ethanol, 1,2-propylene glycol, triacetin, benzyl alcohol and fatty oils and mixtures thereof.

Mixtures

The mixtures according to the invention may contain the individual components in the following amounts:

(a) about 1 to about 99 wt %, preferably about 20 to about 80 wt % and in particular about 30 to about 70 wt % of phenylalkenals of formula (I) and
(b) about 99 to about 1 wt %, preferably about 80 to about 20 wt % and in particular about 70 to about 30 wt % of cooling agents, with the proviso that the amounts stated add up to 100 wt %.

The optional components (c) and (d) may be added, relative to the mixture (a+b), in each case in amounts of each from about 0.1 to about 70 wt %, preferably about 1 to about 60 wt % and in particular about 5 to about 50 wt %.

Industrial Usability

Cosmetic and/or Pharmaceutical Agents Including Oral and Dental Hygiene Products The present invention further relates to cosmetic and/or pharmaceutical preparations and especially oral and dental hygiene products, which contain the mixtures according to the invention preferably in amounts from about 0.0001 to about 20 wt %, especially preferably about 0.0005 to about 10 wt % and in particular about 0.001 to about 5 wt % and more especially preferably 0.001 to about 1 wt %.

These products may contain further typical excipients and additives, such as for example mild surfactants, oils, emulsifiers, nacreous waxes, consistency regulators, thickeners, overfatting agents, stabilizers, polymers, silicone compounds, fats, waxes, lecithins, phospholipids, UV-light protection factors, humectants, biogenic active substances, antioxidants, deodorants, antiperspirants, antidandruff agents, film-forming agents, swelling agents, insect repellents, self-tanning agents, tyrosine inhibitors (depigmenting agents), hydrotropes, solubilizers, preservatives, perfume oils, colorants and the like.

1. Surfactants

Anionic, nonionic, cationic and/or amphoteric or zwitterionic surfactants may be present as surface-active substances, usually in a proportion of about 1 to 70, preferably 5 to 50 and especially 10 to 30 wt %. Typical examples of anionic surfactants are soaps, alkylbenzene sulfonates, alkane sulfonates, olefin sulfonates, alkyl ether sulfonates, glycerol ether sulfonates, α-methylester sulfonates, sulfo fatty acids, alkyl sulfates, alkyl ether sulfates, glycerol ether sulfates, fatty acid ether sulfates, hydroxy-mixed ether sulfates, monoglyceride(ether)sulfates, fatty acid amide(ether)sulfates, mono- and dialkylsulfosuccinates, mono- and dialkylsulfosuccinamates, sulfotriglycerides, amide soaps, ether-carboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl-oligoglucoside sulfates, protein fatty acid condensates (especially wheat-based plant products) and alkyl(ether)phosphates. If the anionic surfactants contain polyglycol ether chains, these may have a conventional, but preferably a narrower homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yloligoglycosides or glucuronic acid derivatives, fatty acid-N-alkylglucamides, protein hydrolyzates (especially wheat-based plant products), polyol fatty acid esters, sugar esters, sorbitan esters, polysorbates and amine oxides. If the nonionic surfactants contain polyglycol ether chains, these may have a conventional, but preferably a narrower homolog distribution. Typical examples of cationic surfactants are quaternary ammonium compounds, for example dimethyldistearylammonium chloride, and ester-quats, especially quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The aforementioned surfactants are known compounds exclusively. Typical examples of especially suitable mild, i.e. especially skin-compatible surfactants are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, α-olefin sulfonates, ether-carboxylic acids, alkyloligoglucosides, fatty acid glucamides, alkylamidobetaines, ampho-acetals and/or protein fatty acid condensates, the latter preferably based on wheat proteins.

2. Oils

As oils, consideration may be given for example to Guerbet alcohols based on fatty alcohols with 6 to 18, preferably 8 to carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, especially 2-ethylhexanol, esters of $C_{18}$-$C_{38}$ alkylhydroxy-carboxylic acids with linear or branched $C_6$-$C_{22}$ fatty alcohols, especially dioctyl malates, esters of linear and/or branched fatty acids with polyhydric alcohols (e.g. propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, e.g. dicaprylyl carbonate (Cetiol® CC), Guerbet carbonates based on fatty alcohols with 6 to 18, preferably 8 to 10 carbon atoms, esters of benzoic acid with linear and/or branched $C_6$-$C_{22}$ alcohols (e.g. Finsolv® TN), linear or branched, symmetric or asymmetric dialkyl ethers with 6 to 22 carbon atoms per alkyl group, e.g. dicaprylyl ether (Cetiol® OE), ring-opening products of epoxidized fatty acid esters with polyols, silicone oils (cyclomethicones, silicon methicone types among others) and/or aliphatic or naphthenic hydrocarbons, such as squalane, squalene or dialkylcyclohexanes.

3. Emulsifiers

As emulsifiers, consideration may be given for example to nonionogenic surfactants from at least one of the following groups:

addition products of 2 to 30 mol ethylene oxide and/or 0 to 5 mol propylene oxide on linear fatty alcohols with 8 to 22 carbon atoms, on fatty acids with 12 to 22 carbon atoms, on alkyl phenols with 8 to 15 carbon atoms in the alkyl group and alkylamines with 8 to 22 carbon atoms in the alkyl residue;

alkyl and/or alkenyl oligoglycosides with 8 to 22 carbon atoms in the alk(en)yl residue and ethoxylated analogs thereof;

addition products of 1 to 15 mol ethylene oxide on castor oil and/or hardened castor oil;

addition products of 15 to 60 mol ethylene oxide on castor oil and/or hardened castor oil;

partial esters of glycerol and/or sorbitan with unsaturated, linear or saturated, branched fatty acids with 12 to 22 carbon atoms and/or hydroxycarboxylic acids with 3 to 18 carbon atoms and adducts thereof with 1 to 30 mol ethylene oxide;

partial esters of polyglycerol (average degree of self-condensation 2 to 8), polyethylene glycol (molecular weight 400 to 5000), trimethylol propane, pentaerythritol, sugar alcohols (e.g. sorbitol), alkyl glucosides (e.g. methyl glucoside, butyl glucoside, lauryl glucoside) and polyglucosides (e.g. cellulose) with saturated and/or unsaturated, linear or branched fatty acids with 12 to 22 carbon atoms and/or hydroxycarboxylic acids with 3 to 18 carbon atoms and adducts thereof with 1 to 30 mol ethylene oxide;

mixed esters of pentaerythritol, fatty acids, citric acid and fatty alcohol and/or mixed esters of fatty acids with 6 to 22 carbon atoms, methylglucose and polyols, preferably glycerol or polyglycerol;

mono-, di- and trialkylphosphates and mono-, di- and/or tri-PEG-alkylphosphates and salts thereof;

wool-wax alcohols;

polysiloxane-polyalkyl-polyether copolymers or corresponding derivatives;

block copolymers e.g. polyethylene glycol-30 dipolyhydroxystearate;

polymer emulsifiers, e.g. Pemulen types (TR-1, TR-2) from Goodrich or Cosmedia® SP from Cognis;

polyalkylene glycols and glycerol carbonate.

Particularly suitable emulsifiers are explained in more detail below:

(i) Alkoxylates. The addition products of ethylene oxide and/or of propylene oxide on fatty alcohols, fatty acids, alkyl phenols or on castor oil are known, commercially available products. These are mixtures of homologs, whose average degree of alkoxylation corresponds to the ratio of the amounts of ethylene oxide and/or propylene oxide and substrate with which the addition reaction is carried out. $C_{12/18}$ fatty acid mono- and diesters of addition products of ethylene oxide on glycerol are known refatting agents for cosmetic preparations.

(ii) Alkyl and/or alkenyl oligoglycoside. Alkyl and/or alkenyl oligoglycosides, their production and their use are known from the prior art. They are produced in particular by reaction of glucose or oligosaccharides with primary alcohols with 8 to 18 carbon atoms. Regarding the glycoside residue, both monoglycosides, in which a cyclic sugar residue is bound by a glycosidic bond to the fatty alcohol, and oligomeric glycosides with a degree of oligomerization preferably up to about 8, are suitable. The degree of oligomerization is a statistical mean value, based on a usual distribution of homologs for these technical products.

(iii) Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof, which may still contain small amounts of triglyceride as byproduct from the production process. Addition products of 1 to 30, preferably 5 to 10 mol ethylene oxide on the stated partial glycerides are also suitable.

(iv) Sorbitan esters. As sorbitan esters, consideration may be given to sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, preferably 5 to 10 mol ethylene oxide on the stated sorbitan esters are also suitable.

(v) Polyglycerol esters. Typical examples of suitable polyglycerol esters are polyglyceryl-2 dipolyhydroxystearates (Dehymuls® PGPH), polyglycerol-3-diisostearates (Lameform® TGI), polyglyceryl-4 isostearates (Isolan® GI 34), polyglyceryl-3 oleates, diisostearoyl polyglyceryl-3 diisostearates (Isolan® PDI), polyglyceryl-3 methylglucose distearates (Tego Care® 450), polyglyceryl-3 beeswax (Cera Bellina®), polyglyceryl-4 caprates (Polyglycerol Caprate T2010/90), polyglyceryl-3 cetyl ethers (Chimexane® NL), polyglyceryl-3 distearates (Cremophor® GS 32) and polyglyceryl polyricinoleates (Admul® WOL 1403) polyglyceryl dimerate isostearates and mixtures thereof. Examples of further suitable polyol esters are the mono-, di- and triesters of trimethylol propane optionally reacted with 1 to 30 mol ethylene oxide or pentaerythritol with lauric acid, coconut fatty acid, tallow fatty acid, palmitic acid, stearic acid, oleic acid, behenic acid and the like.

(vi) Anionic emulsifiers. Typical anionic emulsifiers are aliphatic fatty acids with 12 to 22 carbon atoms, for example palmitic acid, stearic acid or behenic acid, and dicarboxylic acids with 12 to 22 carbon atoms, for example azelaic acid or sebacic acid.

(vii) Amphoteric and cationic emulsifiers. Furthermore, zwitterionic surfactants may be used as emulsifiers. Zwitterionic surfactants are those surface-active compounds that have at least one quaternary ammonium group and at least one carboxylate and one sulfonate group in the molecule. Particularly suitable zwitterionic surfactants are the so-called betaines such as the N-alkyl-N,N-dimethylammonium glycinates, for example coconut alkyldimethylammonium glycinate, N-acylaminopropyl-N,N-dimethylammonium glycinates, for example coconut acylaminopropyldimethylammonium glycinate, and 2-alkyl-3-carboxylmethyl-3-hydroxyethylimidazoline with in each case 8 to 18 carbon atoms in the alkyl or acyl group and coconut acylaminoethylhydroxyethylcarboxymethyl glycinate. The fatty acid amide derivative known by the CTFA designation Cocamidopropyl Betaine is especially preferred. Ampholytic surfactants are also suitable emulsifiers. Ampholytic surfactants are those surface-active compounds which, in addition to a $C_{8/18}$ alkyl or acyl group in the molecule, contain at least one free amino group and at least one —COOH— or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids and alkylaminoacetic acids with in each case about 8 to 18 carbon atoms in the alkyl group. Especially preferred ampholytic surfactants are N-coconut alkylaminopropionate, coconut acylaminoethylaminopropionate and $C_{12/18}$ acyl sarcosine. Finally, cationic surfactants may also be considered as emulsifiers, wherein those of the type of the esterquats, preferably methyl-quaternized difatty acid triethanolamine ester salts, are especially preferred.

4. Fats and Waxes

Typical examples of fats are glycerides, i.e. solid or liquid vegetable or animal products, which consist essentially of mixed glycerol esters of higher fatty acids; waxes that may be considered include, among others, natural waxes, e.g. candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), preen oil, ceresin, ozocerite (earth wax), petrolatum, paraffin waxes, microwaxes; chemically modified waxes (hard waxes), e.g. montan ester waxes, Sasol waxes, hydrogenated jojoba waxes and synthetic waxes, e.g. polyalkylene waxes and polyethylene glycol waxes. In addition to the fats, fat-like substances such as lecithins and phospholipids may also come into consideration as additives. The term lecithins is understood by a person skilled in the art as meaning those glycero-phospholipids that are formed from fatty acids, glycerol, phosphoric acid and choline by esterification. In technical circles lecithins are therefore also often called phosphatidylcholines (PCs). As examples of natural lecithins, we may mention the cephalins, which are also called phosphatidic acids, and are derivatives of 1,2-diacyl-sn-glycerol-3-phosphoric acids. On the other hand, phospholipids are usually understood as mono- and preferably diesters of phosphoric acid with glycerol (glycerol phosphates), which are generally included among the fats. In addition, sphingosines or sphingolipids may also come into consideration.

5. Nacreous Waxes

For example, the following may come into consideration as nacreous waxes: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted carboxylic acids with fatty alcohols with 6 to 22 carbon atoms, especially long-chain esters of tartaric acid; fatty substances, for example fatty alcohols, fatty ketones, fatty aldehydes, fatty ethers and fatty carbonates, which have at least 24 carbon atoms in total, especially laurone and distearyl ether; fatty acids such as stearic acid, hydroxystearic acid or behenic acid, ring-opening products of olefin epoxides with 12 to 22 carbon atoms with fatty alcohols with 12 to 22 carbon atoms and/or polyols with 2 to 15 carbon atoms and 2 to 10 hydroxyl groups and mixtures thereof.

6. Consistency Regulators and Thickening Agents

As consistency regulators, consideration may be given primarily to fatty alcohols or hydroxy fatty alcohols with 12 to 22 and preferably 16 to 18 carbon atoms and in addition partial glycerides, fatty acids or hydroxy fatty acids. A combination of these substances with alkyl-oligoglucosides and/or fatty acid-N-methylglucamides of identical chain length and/or polyglycerol-poly-12-hydroxystearates is preferred. Suitable thickening agents are for example Aerosil types (hydrophilic silicic acids), polysaccharides, especially xanthan gum, guar-guar, agar-agar, alginates and tyloses, carboxymethylcellulose and hydroxyethyl- and hydroxypropylcellulose, other higher-molecular polyethylene glycol mono- and diesters of fatty acids, polyacrylates (e.g. Carbopols® and Pemulen types from Goodrich; Synthalene® from Sigma; Keltrol types from Kelco; Sepigel types from Seppic; Salcare types from Allied Colloids), polyacrylamides, polymers, polyvinyl alcohol and polyvinylpyrrolidone. Bentonites, e.g. Bentone® Gel VS-5PC (Rheox), which is a mixture of cyclopentasiloxane, disteardimonium hectorite and propylene carbonate, have also proved to be especially effective. Consideration may also be given to surfactants, for example ethoxylated fatty acid glycerides, esters of fatty acids with polyols such as for example pentaerythritol or trimethylol propane, fatty alcohol ethoxylates with a narrower distribution of homologs or alkyl-oligoglucosides and electrolytes such as common salt and ammonium chloride.

7. Overfatting Agents and Stabilizers

Substances such as for example lanolin and lecithin and polyethoxylated or acylated lanolin and lecithin derivatives, polyol fatty acid esters, monoglycerides and fatty acid alkanolamides may be used as overfatting agents, the latter serving simultaneously as foam stabilizers.

Metal salts of fatty acids, e.g. magnesium, aluminum and/or zinc stearate or ricinoleate, may be used as stabilizers.

8. Polymers

Suitable cationic polymers are for example cationic cellulose derivatives, e.g. a quaternized hydroxyethylcellulose, which is available under the designation Polymer JR 400® from Amerchol, cationic starch, copolymers of diallylammonium salts and acrylamides, quaternized vinylpyrrolidone/vinylimidazole polymers, e.g. Luviquat® (BASF), condensation products of polyglycols and amines, quaternized collagen polypeptides, for example Lauryldimonium Hydroxypropyl Hydrolyzed Collagen (Lamequat® L/Grünau), quaternized wheat polypeptides, polyethyleneimine, cationic silicone polymers, e.g. amodimethicones, copolymers of adipic acid and dimethylaminohydroxypropyl diethylenetriamine (Cartaretine®/Sandoz), copolymers of acrylic acid with dimethyl-diallylammonium chloride (Merquat® 550/Chemviron), polyaminopolyamides and crosslinked water-soluble polymers thereof, cationic chitin derivatives such as for example quaternized chitosan, optionally with microcrystalline distribution, condensation products from dihaloalkylene, e.g. dibromobutane with bis-dialkylamines, e.g. bis-dimethylamino-1,3-propane, cationic guar gum, e.g. Jaguar® CBS, Jaguar® C-17, Jaguar® C-16 from the company Celanese, quaternized ammonium-salt polymers, e.g. Mirapol® A-15, Mirapol® AD-1, Mirapol® AZ-1 from the company Miranol.

As anionic, zwitterionic, amphoteric and nonionic polymers, consideration may be given for example to vinyl acetate/crotonic acid copolymers, vinylpyrrolidone/vinylacrylate copolymers, vinyl acetate/butyl maleate/isobornyl acrylate copolymers, methylvinyl ether/maleic acid anhydride copolymers and esters thereof, uncrosslinked and polyol-crosslinked polyacrylic acids, acrylamidopropyltrimethylammonium chloride/acrylate copolymers, octylacrylamide/methylmethacrylate/tert.butyl-aminoethylmethacrylate/2-hydroxypropylmethacrylate copolymers, polyvinylpyrrolidone, vinylpyrrolidone/vinyl acetate copolymers, vinylpyrrolidone/dimethylaminoethylmethacrylate/vinyl caprolactam terpolymers and optionally derivatized cellulose ethers and silicones.

9. Silicone Compounds

Suitable silicone compounds are for example dimethylpolysiloxanes, methylphenyl polysiloxanes, cyclic silicones and amino-, fatty acid-, alcohol-, polyether-, epoxy-, fluoro-, glycoside- and/or alkyl-modified silicone compounds, which may be both liquid and resinous at room temperature. Others that are suitable are simethicones, which are mixtures of dimethicones with an average chain length from 200 to 300 dimethylsiloxane units and hydrogenated silicates.

10. UV-Light Protection Factors

UV-light protection factors mean, for example, organic substances that are liquid or crystalline at room temperature (light protection filters), which are able to absorb ultraviolet radiation and give up the absorbed energy in the form of longer-wave radiation, e.g. heat. Usually the UV-light protection factors are present in amounts from 0.1 to 5 and preferably 0.2 to 1 wt %. UVB filters may be oil-soluble or water-soluble. As oil-soluble substances, we may for example mention:

3-benzylidene camphor or 3-benzylidene norcamphor and derivatives thereof, e.g. 3-(4-methylbenzylidene)camphor;

4-aminobenzoic acid derivatives, preferably 4-(dimethylamino)benzoic acid-2-ethylhexyl esters, 4-(dimethylamino)benzoic acid-2-octyl esters and 4-(dimethylamino)benzoic acid amyl esters;

esters of cinnamic acid, preferably 4-methoxycinnamic acid-2-ethylhexyl esters, 4-methoxycinnamic acid propyl esters, 4-methoxycinnamic acid isoamyl esters, 2-cyano-3,3-phenylcinnamic acid-2-ethylhexyl esters (octocrylenes);

esters of salicylic acid, preferably salicylic acid-2-ethylhexyl esters, salicylic acid-4-isopropylbenzyl esters, salicylic acid homomenthyl esters;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzomalonic acid di-2-ethylhexyl esters;

triazine derivatives, e.g. 2,4,6-trianilino-(p-carbo-2'-ethyl-1'-hexyloxy)-1,3,5-triazine and octyl triazone or dioctyl butamido triazone (Uvasorb® HEB);

propane-1,3-diones, e.g. 1-(4-tert.-butylphenyl)-3-(4'-methoxyphenyl)propane-1,3-dione;

ketotricyclo(5.2.1.0)decane derivatives.

Consideration may be given to the following as water-soluble substances:

2-phenylbenzimidazole-5-sulfonic acid and alkali, alkaline-earth, ammonium, alkylammonium, alkanolammonium and glucammonium salts thereof;

1H-benzimidazole-4,6-disulfonic acid, 2,2'-(1,4-phenylene)bis-, disodium salt (Neo Heliopan® AP)

sulfonic acid derivatives of benzophenones, preferably 2-hydroxy-4-methoxybenzophenone-5-sulfonic acid and salts thereof;

sulfonic acid derivatives of 3-benzylidene camphor, e.g. 4-(2-oxo-3-bornylidene methyl)benzenesulfonic acid and 2-methyl-5-(2-oxo-3-bornylidene)sulfonic acid and salts thereof.

As typical UV-A filters, consideration may be given in particular to derivatives of benzoyl methane, for example 1-(4'-tert.-butylphenyl)-3-(4'-methoxyphenyl)propane-1,3-dione, 4-tert.-butyl-4'-methoxydibenzoyl methane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione and enamine compounds. The UV-A and UV-B filters may of course also be used in mixtures. Especially favorable combinations consist of the derivatives of benzoyl methane, e.g. 4-tert.-butyl-4'-methoxydibenzoyl methane (Parsol® 1789) and 2-cyano-3,3-phenylcinnamic acid-2-ethylhexyl ester (Octocrylenes) in combination with cinnamic acid ester, preferably 4-methoxycinnamic acid-2-ethylhexyl ester and/or 4-methoxycinnamic acid propyl ester and/or 4-methoxycinnamic acid isoamyl ester. Advantageously, such combinations are combined with water-soluble filters, e.g. 2-phenylbenzimidazole-5-sulfonic acid and alkali, alkaline-earth, ammonium, alkylammonium, alkanolammonium and glucammonium salts thereof.

In addition to the aforementioned soluble substances, insoluble light-protection pigments, namely finely divided metal oxides or salts, may also be considered for this purpose. Examples of suitable metal oxides are in particular zinc oxide and titanium dioxide and in addition oxides of iron, zirconium, silicon, manganese, aluminum and cerium and mixtures thereof. Silicates (talc), barium sulfate or zinc stearate may be used as salts. The oxides and salts are used in the form of pigments for skin-care and skin-protection emulsions and decorative cosmetics. The particles should then have an average diameter of less than 100 nm, preferably between 5 and 50 nm and especially between 15 and 30 nm. They may have a spherical shape, but it is also possible to use particles that have an ellipsoidal shape or a shape deviating in some other way from spherical. The pigments may also have been surface-treated, i.e. made hydrophilic or hydrophobic. Typical examples are coated titanium dioxides, e.g. titanium dioxide T 805 (Degussa) or Eusolex® T2000, Eusolex® T, Eusolex® T-ECO, Eusolex® T-S, Eusolex® T-Aqua, Eusolex® T-45D (all Merck), Uvinul TiO₂ (BASF). Mainly silicones and especially trialkoxyoctylsilanes or simethicones come into consideration as hydrophobic coating agents. So-called micro- or nanopigments are preferably used in sunscreen agents. Micronized zinc oxide e.g. Z-COTE® or Z-COTE HP1® is preferably used.

11. Humectants

Humectants serve for further optimization of the sensory properties of the composition and for moisture control of the skin. At the same time, the low-temperature stability of the preparations according to the invention, especially in the case of emulsions, is increased. The humectants are usually contained in an amount from 0.1 to 15 wt %, preferably 1 to 10 wt %, and especially 5 to 10 wt %.

The following, among others, are suitable according to the invention: amino acids, pyrrolidone carboxylic acid, lactic acid and salts thereof, lactitol, urea and urea derivatives, uric acid, glucosamine, creatinine, cleavage products of collagen, chitosan or chitosan salts/derivatives, and especially polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (including fructose, glucose, maltose, maltitol, mannitol, inositol, sorbitol, sorbityl silanediol, sucrose, trehalose, xylose, xylitol, glucuronic acid and salts thereof), ethoxylated sorbitol (sorbeth-6, sorbeth-20, sorbeth-30, sorbeth-40), honey and hardened honey, hardened starch hydrolyzates and mixtures of hardened wheat protein and PEG-20-acetate copolymer. Glycerol, diglycerol, triglycerol and butylene glycol are especially suitable as humectants according to the invention.

12. Biogenic Active Substances and Antioxidants

Biogenic active substances are to be understood as including for example tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, e.g. prunus extract, bambara groundnut extract and vitamin complexes.

Antioxidants interrupt the photochemical reaction chain that is triggered when UV radiation penetrates into the skin. Typical examples are amino acids (e.g. glycine, histidine, tyrosine, tryptophan) and derivatives thereof, imidazoles (e.g. urocaninic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionin sulfoximines, homocysteine sulfoximine, buthionin sulfones, penta-, hexa-, heptathionin sulfoximine) in very small compatible dosages (e.g. pmol to μmol/kg), other (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbylphosphate, ascorbyl acetate), tocopherols and derivatives (e.g. vitamin-E-acetate), vitamin A and derivatives (vitamin-A-palmitate) and coniferyl benzoate of gum benzoin, rutinic acid and derivatives thereof, α-glycosylrutin, ferulic acid, furfurylidene glucitol, carnosine, butylated hydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$), selenium and derivatives thereof (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of the aforementioned active substances that are suitable according to the invention.

13. Deodorants and Antimicrobial Agents

Cosmetic deodorants counteract body odors, masking or removing them. Body odors arise through the action of skin bacteria on apocrine sweat, wherein degradation products with an unpleasant odor are formed. Accordingly, deodorants contain active substances that function as antimicrobial agents, enzyme inhibitors, odor absorbers or odor masking agents.

(i) Antimicrobial Agents. Basically all substances that are effective against gram-positive bacteria are suitable as antimicrobial agents, for example 4-hydroxybenzoic acid and salts and esters thereof, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylene-bis(6-bromo-4-chlorophenol), 3-methyl-4-(1-methylethyl)-phenol, 2-benzyl-4-chlorophenol, 3-(4-chlorophenoxy)-1,2-propanediol, 3-iodo-2-propinylbutylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides, e.g. salicylic acid-n-octylamide or salicylic acid-n-decylamide.

(ii) Enzyme inhibitors. Esterase inhibitors for example are suitable as enzyme inhibitors. These are preferably trialkyl citrates such as trimethyl citrate, tripropyl citrate, triisopropyl citrate, tributyl citrate and especially triethyl citrate (Hydagen® CAT). The substances inhibit enzyme activity and thereby reduce the formation of odors. Other substances that may come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl esters, glutaric acid diethyl esters, adipic acid, adipic acid monoethyl esters, adipic acid diethyl esters, malonic acid and malonic acid diethyl esters, hydroxycarboxylic acids and esters thereof, for example citric acid, malic acid, tartaric acid or tartaric acid diethyl esters, and zinc glycinate.

(iii) Odor absorbers. Substances that can absorb and largely retain odor-forming compounds are suitable as odor absorbers. They lower the partial pressure of the individual components and thus also reduce their rate of propagation. What is important is that perfumes must remain unaffected. Odor absorbers do not have any efficacy against bacteria. For example, their main constituent is a complex zinc salt of ricinoleic acid or special, largely odor-neutral odorants, which a person skilled in the art knows as "fixatives", e.g. extracts of labdanum or styrax or certain abietic acid derivatives. Fragrances or perfume oils function as odor masking agents, and in addition to their function as odor masking agents they endow the deodorants with their particular perfume note. For example, mixtures of natural and synthetic fragrances may be mentioned as perfume oils. Natural fragrances are extracts from blossoms, stems and leaves, fruit, peel, roots, wood, herbs and grasses, needles and branches and resins and balsams. Furthermore, animal raw materials may come into consideration, for example civet and castoreum. Typical synthetic fragrance compounds are products of the type of esters, ethers, aldehydes, ketones, alcohols and hydrocarbons. Fragrance compounds of the ester type are e.g. benzyl acetate, p-tert.-butylcyclohexyl acetate, linalyl acetate, phenylethyl acetate, linalyl benzoate, benzyl formate, allylcyclohexyl propionate, styralyl propionate and benzylsalicylate. The ethers include for example benzylethyl ether, and the aldehydes include e.g. the linear alkanals with 8 to 18 carbon atoms, citral, citronellal, citronellyl oxyacetaldehyde, cyclamen aldehyde, hydroxycitronellal, lilial and bourgeonal, the ketones include e.g. the ionones and methyl cedryl ketone, the alcohols include anethole, citronellol, eugenol, isoeugenol, geraniol, linalool, phenylethyl alcohol and terpineol, the hydrocarbons include mainly the terpenes and balsams. Preferably, however, mixtures of various fragrances are used, which together produce an attractive perfume note. Essential oils of lower volatility, which are mostly used as flavor components, are also suitable as perfume oils, e.g. sage oil, chamomile oil, clove oil, melissa oil, mint oil, cinnamon leaf oil, lime blossom oil, juniper berry oil, vetiver oil, olibanum oil, galbanum oil, labdanum oil and lavandin oil. Preferably, bergamot oil, dihydromyrcenol, lilial, lyral, citronellol, phenylethyl alcohol, α-hexyl cinnamaldehyde, geraniol, benzyl acetone, cyclamen aldehyde, linalool, Boisambrene Forte, ambroxan, indol, hedions, sandelice, lemon oil, mandarin oil, orange oil, allylamyl glycolate, cyclovertal, lavandin oil, muscatel sage oil, β-damascone, geranium oil bourbon, cyclohexylsalicylate, Vertofix Coeur, Iso-E-Super, Fixolide NP, Evernyl, Iraldein gamma, phenylacetic acid, geranyl acetate, benzyl acetate, rose oxide, romilat, irotyl and floramat are used, alone or in mixtures.

(iv) Antiperspirants. Antiperspirants reduce the formation of sweat by influencing the activity of the ecrine sweat glands, and thus counteract underarm dampness and body odor. Aqueous or water-free formulations of antiperspirants typically contain the following ingredients:
astringent substances,
oil components,
non-ionic emulsifiers,
coemulsifiers,
consistency regulators,
excipients, e.g. thickeners or complexing agents and/or
non-aqueous solvents, e.g. ethanol, propylene glycol and/or glycerol.

Salts of aluminum, zirconium or zinc are mainly suitable as astringent antiperspirant active substances. Suitable substances with antisudorific action are e.g. aluminum chloride, aluminum hydrochloride, aluminum dihydrochloride, aluminum sesquihydrochloride and complex compounds thereof, e.g. with propylene glycol-1,2, aluminum hydroxyallantoinate, aluminum chloride tartrate, aluminum-zirconium trihydrochloride, aluminum-zirconium tetrahydrochloride, aluminum-zirconium pentahydrochloride and complex compounds thereof, e.g. with amino acids such as glycine. In addition, antiperspirants may contain smaller amounts of usual oil-soluble and water-soluble excipients. These oil-soluble excipients may be for example:
anti-inflammatory, skin-protecting or fragrant essential oils,
synthetic skin-protecting active substances and/or
oil-soluble perfume oils.

Usual water-soluble additives are e.g. preservatives, water-soluble odorants, pH adjusters, e.g. buffer mixtures, water-soluble thickening agents, e.g. water-soluble natural or synthetic polymers such as xanthan gum, hydroxyethylcellulose, polyvinylpyrrolidone or high-molecular polyethylene oxides.

14. Film-Forming Agents

Usual film-forming agents are for example chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid or salts thereof and similar compounds.

15. Antidandruff Active Substances

As antidandruff active substances, consideration may be given to piroctone olamine (1-hydroxy-4-methyl-6-(2,4,4-trimethylpentyl)-2-(1H)-pyridinone monoethanolamine salt), Baypival® (climbazole), Ketoconazol®, (4-acetyl-1-{-4-[2-(2,4-dichlorophenyl) r-2-(1H-imidazol-1-ylmethyl)-1,3-dioxylan-c-4-ylmethoxyphenyl)piperazine, ketoconazole, elubiol, selenium disulfide, colloidal sulfur, sulfur polyethylene glycol sorbitan monooleate, sulfur ricinolpolyethoxylate, sulfur-tar distillates, salicylic acid (possibly in combination with hexachlorophene), undecylenic acid monoethanolamide sulfosuccinate Na salt, Lamepon® UD (protein-undecylenic acid condensate), zinc pyrithione, aluminum pyrithione and magnesium pyrithione/dipyrithione-magnesium sulfate.

16. Swelling Agents

Montmorillonites, clay mineral substances, Pemulen and alkyl-modified Carbopol types (Goodrich) may serve as swelling agents for aqueous phases. Other suitable polymers or swelling agents are given in the review by R.Lochhead in Cosm.Toil. 108, 95 (1993).

17. Insect Repellents

N,N-Diethyl-m-toluamide, 1,2-pentanediol or ethyl-butyl-acetyl-aminopropionate may come into consideration as insect repellents. Dihydroxyacetone is suitable as a self-tanning agent. As tyrosine inhibitors, which prevent the formation of melanin and find application in depigmenting agents, consideration may be given for example to arbutin, ferulic acid, kojic acid, coumaric acid and ascorbic acid (vitamin C).

18. Ingredients for Oral and Dental Hygiene Products

Toothpastes or tooth creams are generally understood to be gel-like or pasty preparations made from water, thickening agents, humectants, abrasive or scouring media, surfactants, sweeteners, aroma substances, deodorizing substances and active substances against oral and dental diseases. All usual scouring media, e.g. chalk, dicalcium phosphate, insoluble sodium metaphosphate, aluminum silicates, calcium pyrophosphate, finely divided synthetic resins, silicic acids, aluminum oxide and aluminum oxide trihydrate, may be used in the toothpastes according to the invention.

Scouring media preferably suitable for the toothpastes according to the invention are in particular finely divided xerogel silicic acids, hydrogel silicic acids, precipitated silicic acids, aluminum oxide trihydrate and finely divided alpha-aluminum oxide or mixtures of these scouring media in amounts from 15 to 40 wt % of the toothpaste. Mainly low-molecular polyethylene glycols, glycerol, sorbitol or mixtures of these products in amounts of up to 50 wt % may come into consideration as humectants. Among the known thickening agents, the thickening, finely divided gel-silicic acids and hydrocolloids, e.g. carboxymethylcellulose, hydroxyethylcellulose, hydroxypropyl guar, hydroxyethyl starch, polyvinylpyrrolidone, high-molecular polyethylene glycol, vegetable gums such as tragacanth, agar-agar, carrageen, gum arabic, xanthan gum and carboxyvinyl polymers (e.g. Carbopol® types) are suitable. In addition to the mixtures of menthofuran and menthol compounds, the oral and dental hygiene products may in particular contain surface-active substances, preferably anionic and nonionic high-foaming surfactants, such as the substances already mentioned above, but especially alkyl ether sulfate salts, alkylpolyglucosides and mixtures thereof.

Further usual toothpaste additives are:
preservatives and antimicrobial substances, e.g. p-hydroxybenzoic acid methyl, ethyl or propyl esters, sodium sorbate, sodium benzoate, bromochlorophene, phenylsalicylic acid esters, thymol and the like;
anticalculus agents, e.g. organophosphates such as 1-hydroxyethane-1,1-diphosphonic acid, 1-phosphone-propane-1,2,3-tricarboxylic acid and others that are known for example from U.S. Pat. No. 3,488,419, DE 2224430 A1 and DE 2343196 A1;
other caries-inhibiting substances, e.g. sodium fluoride, sodium monofluorophosphate, tin fluoride;
sweetening agents, e.g. saccharin-sodium, sodium-cyclamate, sucrose, lactose, maltose, fructose or Apartam®, (L-aspartyl-L-phenylalanine methyl ester), Stevia extracts or sweetening constituents thereof, especially rebaudiosides;
additional flavorings, e.g. eucalyptus oil, anise oil, fennel oil, caraway oil, methyl acetate, cinnamaldehyde, anethole, vanillin, thymol and mixtures of these and other natural and synthetic flavorings;
pigments, e.g. titanium dioxide;
dyes;
buffer substances, e.g. primary, secondary or tertiary alkali phosphates or citric acid/sodium citrate;
wound-healing and anti-inflammatory agents, e.g. allantoin, urea, azulene, chamomile active substances and acetylsalicylic acid derivatives.

Toothpastes in the form of an aqueous, pasty dispersion, containing polishing agents, humectants, viscosity regulators and optionally further usual components, and which contain the mixture of menthofuran and menthol compounds in amounts from 0.5 to 2 wt %, are a preferred embodiment of the cosmetic preparations.

In mouthwashes, combination with aqueous-alcoholic solutions of varying concentration of essential oils, emulsifiers, astringent and toning drug extracts, calculus-inhibiting, antibacterial additives and flavor correctants is directly possible. Another preferred embodiment of the invention is a mouthwash in the form of an aqueous or aqueous-alcoholic solution containing the mixture of menthofuran and menthol compounds in amounts from 0.5 to 2 wt %. In mouthwashes that are diluted before use, adequate effects may be achieved with higher concentrations, corresponding to the proposed dilution ratio.

19. Hydrotropes

To improve the flow behavior, in addition hydrotropes may be used, for example ethanol, isopropyl alcohol, or polyols; these substances largely correspond to the vehicles described at the beginning. Polyols that may be considered here preferably have 2 to 15 carbon atoms and at least two hydroxyl groups. The polyols may also contain other functional groups, especially amino groups, or may be modified with nitrogen. Typical examples are glycerol;
alkylene glycols, for example ethylene glycol, diethylene glycol, propylene glycol, butylene glycol, hexylene glycol and polyethylene glycols with an average molecular weight from 100 to 1000 dalton;
technical oligoglycerol mixtures with a degree of self-condensation from 1.5 to 10, for instance technical diglycerol mixtures with a diglycerol content from 40 to 50 wt %;
methylol compounds, such as in particular trimethylol ethane, trimethylol propane, trimethylol butane, pentaerythritol and dipentaerythritol;
lower alkyl glucosides, especially those with 1 to 8 carbons in the alkyl residue, for example methyl and butyl glucoside;
sugar alcohols with 5 to 12 carbon atoms, for example sorbitol or mannitol,
sugars with 5 to 12 carbon atoms, for example glucose or sucrose;
amino sugars, for example glucamine;
dialcoholamines, such as diethanolamine or 2-amino-1,3-propanediol.

20. Preservatives

Suitable preservatives are for example phenoxyethanol, formaldehyde solution, parabens, pentanediol or sorbic acid and the silver complexes known under the designation Surfacine® and the other classes of substances listed in Appendix 6, Part A and B of the Cosmetics Regulations.

21. Colorants

The colorants used may be the substances that are suitable and approved for cosmetic purposes. Examples are Cochineal Red A (C.I. 16255), Patent Blue V (C.I. 42051), Indigotin (C.I. 73015), Chlorophyllin (C.I. 75810), Quinoline Yellow (C.I. 47005), Titanium Dioxide (C.I. 77891), Indanthrene Blue RS (C.I. 69800) and Madder Lake (C.I. 58000). Luminol may also be present as a luminescent dye. These colorants are usually employed in concentrations from 0.001 to 0.1 wt %, relative to the total mixture.

The total proportion of the excipients and additives may be 1 to 50, preferably 5 to 40 wt %, relative to the agents. The agents may be produced by usual cold or hot processes; the procedure is preferably based on the phase inversion temperature method.

Foodstuffs

The invention further relates to foodstuffs, which contain the mixtures according to the invention preferably in amounts from about 0.5 to about 20 wt %, especially preferably about 1 to about 15 wt % and in particular about 2 to about 10 wt %.

The oral preparations are preferably baked products, for example bread, cookies, cakes, other pastries, confectionery (for example chocolates, chocolate bar products, other bar products, fruit gums, hard and soft toffees, chewing gum), alcoholic or nonalcoholic beverages (for example coffee, tea, iced tea, wine, wine-containing beverages, beer, beer-containing beverages, liqueurs, spirits, brandies, (carbonized) fruit-containing lemonades, (carbonized) isotonic beverages, (carbonized) cold drinks, nectars, soda-water drinks, fruit and vegetable juices, fruit or vegetable juice preparations, instant beverages (for example instant cocoa beverages, instant tea beverages, instant coffee beverages, instant fruit beverages), meat products (for example ham, sausage or raw-sausage preparations, spiced or marinated fresh or salted meat products), eggs or egg products (dried egg, egg white, egg yolk), cereal products (for example breakfast cereals, muesli bars, prefermented ready-to-use rice products), milk products (for example milk drinks, buttermilk drinks, milk-based ice cream, yoghurt, kefir, fresh cheese, soft cheese, hard cheese, dry milk powder, whey, whey beverages, butter, buttermilk, partially or fully hydrolyzed lactoprotein-containing products), products from soybean protein or other soybean fractions (for example soybean milk and products prepared therefrom, fruit drinks with soybean protein, soybean lecithin-containing preparations, fermented products such as tofu or tempeh or products prepared therefrom), products from other plant protein sources, for example oat-protein beverages, fruit preparations (for example jams, fruit ice cream, fruit sauces, fruit fillings), vegetable preparations (for example ketchup, sauces, dried vegetables, frozen vegetables, prefermented vegetables, preserved vegetables), nibbles (for example baked or fried potato chips or potato dough products, extruded products based on corn or peanuts), fat- and oil-based products or emulsions thereof (for example mayonnaise, tartar sauce, dressings), other ready-meals and soups (for example dried soups, instant soups, prefermented soups), spices, spice mixtures and especially seasonings, which for example find application in the snack area.

Chewing Gums

The mixtures according to the invention may also find application in chewing gum preparations. Chewing gums may be classified, depending on the composition, as oral and dental hygiene products (medicinal chewing gums) or as semiluxury foods and thus as a subset of foodstuffs. The amount of the mixtures according to the invention may be between about 0.5 and about 5 wt %, preferably about 1 to 3 about 3 wt % and in particular about 1.5 to 2.5 wt %.

Chewing gums typically contain a water-insoluble and a water-soluble component. The water-insoluble base, which is also called "gum base", usually comprises natural or synthetic elastomers, resins, fats and oils, plasticizers, fillers, colorants and optionally waxes. The proportion of the base in the total composition usually comes to 5 to 95, preferably 10 to 50 and especially 20 to 35 wt %. In a typical embodiment of the invention, the base consists of 20 to 60 wt % of synthetic elastomers, 0 to 30 wt % of natural elastomers, 5 to 55 wt % of plasticizers, 4 to 35 wt % of fillers and minor amounts of additives such as colorants, antioxidants and the like taken together, with the proviso that in any case they are water-soluble in small amounts.

Suitable synthetic elastomers are for example polyisobutylenes with average molecular weights (according to GPC) from 10 000 to 100 000 and preferably 50 000 to 80 000, isobutylene-isoprene copolymers ("butyl elastomers"), styrene-butadiene copolymers (styrene:butadiene ratio e.g. 1:3 to 3:1), polyvinyl acetates with average molecular weights (according to GPC) from 2000 to 90 000 and preferably 10 000 to 65 000, polyisoprenes, polyethylene, vinyl acetate-vinyl laurate copolymers and mixtures thereof. Examples of suitable natural elastomers are rubber such as smoke-dried or liquid latex or guayule and natural gums such as jelutong, lechi caspi, perillo, sorva, massaranduba balata, massaranduba chocolate, nispero, rosindinba, chicle, gutta hang kang and mixtures thereof. Selection of the synthetic and natural elastomers and the mixture proportions thereof is based essentially on whether or not it should be possible to produce bubbles with the chewing gums ("bubble gums"). Preferably, elastomer mixtures are used that contain jelutong, chicle, sorva and massaranduba.

In most cases the elastomers prove too hard or insufficiently deformable during processing, so that it has proved advantageous to use special plasticizers as well, which of course must in particular also meet all the requirements for authorization as food additives. In this respect, mainly esters of resin acids may come into consideration, for example esters of lower aliphatic alcohols or polyols with fully or partially hardened, monomeric or oligomeric resin acids. In particular, the methyl, glycerol, or pentaerythritol esters and mixtures thereof are used for this purpose. Alternatively, consideration may also be given to terpene resins, which may be derived from alpha-pinene, beta-pinene, delta-limonene or mixtures thereof.

Possible fillers or texture agents are magnesium or calcium carbonate, ground pumice stone, silicates, especially magnesium or aluminum silicates, clays, aluminum oxides, talc, titanium dioxide, mono-, di- and tricalcium phosphate and cellulose polymers.

Suitable emulsifiers are tallow, hardened tallow, hardened or partially hardened vegetable oils, cocoa butter, partial glycerides, lecithin, triacetin and saturated or unsaturated fatty acids with 6 to 22 and preferably 12 to 18 carbon atoms and mixtures thereof.

As colorants and whitening agents, consideration may be given for example to the FD & C types permitted for coloring foodstuffs, plant and fruit extracts and titanium dioxide.

The base pastes may contain waxes or may be wax-free; examples of wax-free compositions are given inter alia in the patent document U.S. Pat. No. 5,286,500, the contents of which are expressly referred to herewith.

In addition to the water-insoluble gum base, chewing gum preparations regularly contain a water-soluble component, which is formed for example from softeners, sweeteners, fillers, flavorings, flavor enhancers, emulsifiers, colorants, acidifiers, antioxidants and the like, in this case with the proviso that the component parts possess at least sufficient water solubility. Depending on the water solubility of the particular representatives, individual constituents may accordingly belong both to the water-insoluble and to the water-soluble phase. It is, however, also possible to use combinations for example of a water-soluble and a water-insoluble emulsifier, wherein the individual representatives are then located in different phases. Usually the water-insoluble component makes up 5 to 95 and preferably 20 to 80 wt % of the preparation.

Water-soluble softeners or plasticizing agents are added to the chewing gum compositions in order to improve the chewability and the chewing feel, and are present in the mixtures typically in amounts from 0.5 to 15 wt %. Typical examples are glycerol, lecithin and aqueous solutions of sorbitol, hardened starch hydrolyzates or corn syrup.

Sweeteners that may be considered are both sugar-containing and sugar-free compounds, which are used in amounts from 5 to 95, preferably 20 to 80 and especially 30 to 60 wt % relative to the chewing gum composition. Typical saccharide sweeteners are sucrose, dextrose, maltose, dextrin, dried invert sugar, fructose, levulose, galactose, corn syrup and mixtures thereof. Sugar substitutes that may be considered are sorbitol, mannitol, xylitol, hardened starch hydrolyzates, maltitol and mixtures thereof. As additives, consideration may also be given to so-called HIAS ("high intensity artificial sweeteners"), for example sucralose, aspartame, acesulfame salts, alitame, saccharin and saccharin salts, cyclamic acid and salts thereof, glycyrrhizins, dihydrochalcone, thaumatin, monellin and the like, alone or in mixtures. The hydrophobic HIAS, which are the object of international patent application WO 2002 091849 A1 (Wrigleys) and stevia extracts and active constituents thereof, especially rebaudioside A, are also particularly effective. The amount of these substances used depends primarily on their performance and is typically in the range from 0.02 to 8 wt %.

Fillers such as for example polydextrose, Raftilose, Raftiline, fructooligosaccharides (NutraFlora), Palatinose oligosaccharides, guar gum hydrolyzate (Sun Fiber) and dextrins are suitable in particular for the manufacture of low-calorie chewing gums.

The choice of other flavorings is practically limitless and is not critical to the essence of the invention. Usually the total proportion of all flavorings is 0.1 to 15 and preferably 0.2 to 5 wt % relative to the chewing gum composition. Suitable additional flavorings are for example essential oils, synthetic flavorings and the like, such as anise oil, star anise oil, caraway oil, eucalyptus oil, fennel oil, lemon oil, wintergreen oil, clove oil, and the like, such as are also used for example in oral and dental hygiene products.

The chewing gums may moreover contain excipients and additives that are suitable for example for dental hygiene, especially for combating plaque and gingivitis, e.g. chlorhexidine, CPC or triclosan. They may also contain pH-regulators (e.g. buffers or urea), active substances against caries (e.g. phosphates or fluorides), biogenic active substances (antibodies, enzymes, caffeine, plant extracts), provided these substances are permitted for foodstuffs and do not have any undesirable interactions with one another.

Flavor and Perfume Preparations

The invention further relates to flavor and perfume preparations that contain the mixtures according to the invention preferably in amounts from about 0.005 to about 50 wt %, especially preferably about 0.01 to about 40 wt % and in particular about 0.1 to about 30 wt %.

As perfume oils, we may mention mixtures of natural and synthetic fragrances. Natural fragrances are extracts of blossoms (lily, lavender, rose, jasmine, neroli, ylang-ylang), stems and leaves (geranium, patchouli, petitgrain), fruits (anise, coriander, caraway, juniper), peel (bergamot, lemon, orange), roots (mace, angelica, celery, cardamom, costus, iris, calamus), wood (pine, sandalwood, guaiac, cedar, rose wood), herbs and grasses (tarragon, lemongrass, sage, thyme), needles and branches (spruce, fir, pine, mountain pine), resins and balsams (galbanum, elemi, benzin, myrrh, olibanum, opopanax). Animal raw materials may also come into consideration, for example civet and castoreum. Typical synthetic fragrance compounds are products of the type of esters, ethers, aldehydes, ketones, alcohols and hydrocarbons. Fragrance compounds of the ester type are e.g. benzyl acetate, phenoxyethylisobutyrate, p-tert.-butylcyclohexyl acetate, linalyl acetate, dimethylbenzylcarbinyl acetate, phenylethyl acetate, linalyl benzoate, benzyl formate, ethylmethylphenylglycinate, allylcyclohexyl propionate, styrallyl propionate and benzylsalicylate. The ethers include for example benzylethyl ether, the aldehydes include e.g. the linear alkanals with 8 to 18 carbon atoms, citral, citronellal, citronellyloxyacetaldehyde, cyclamen aldehyde, hydroxycitronellal, lilial and bourgeonal, the ketones include e.g. the ionones, α-isomethylionone and methylcedryl ketone, the alcohols include anethole, citronellol, eugenol, isoeugenol, geraniol, linalool, phenylethyl alcohol and terpineol, the hydrocarbons include mainly the terpenes and balsams. Preferably, however, mixtures of various fragrances are used, which together produce an attractive perfume note. Essential oils of lower volatility, which are mostly used as flavor components, are also suitable as perfume oils, e.g. sage oil, chamomile oil, clove oil, melissa oil, mint oil, cinnamon leaf oil, lime blossom oil, juniper berry oil, vetiver oil, olibanum oil, galbanum oil, labolanum oil and lavandin oil. Preferably bergamot oil, dihydromyrcenol, lilial, lyral, citronellol, phenylethyl alcohol, α-hexyl cinnamaldehyde, geraniol, benzyl acetone, cyclamen aldehyde, linalool, Boisambrene Forte, ambroxan, indol, hedions, sandelice, lemon oil, mandarin oil, orange oil, allylamyl glycolate, cyclovertal, lavandin oil, muscatel sage oil, β-damascone, geranium oil bourbon, cyclohexylsalicylate, Vertofix Coeur, Iso-E-Super, Fixolide NP, Evernyl, Iraldein gamma, phenylacetic acid, geranyl acetate, benzyl acetate, rose oxide, romilat, irotyl and floramat, are used, alone or in mixtures.

For example peppermint oil, spearmint oil, anise oil, star anise oil, caraway oil, eucalyptus oil, fennel oil, lemon oil, wintergreen oil, clove oil and the like may come into consideration as flavorings.

Method and Uses

The invention further relates to a method for intensifying the cooling effect of physiological cooling agents comprising mixing a mixture according to the invention with one of the aforementioned preparations.

The invention further comprises the use of compounds of formula (I)
- for intensifying the cooling effect, the freshness and the impact of physiological cooling agents,
- for intensifying the impression of freshness, the menthol taste or peppermint taste of cosmetic preparations, oral hygiene products, pharmaceutical preparations, foodstuffs and flavoring or perfume preparations,
- for reducing the bitterness of physiological cooling agents and
- for producing and/or intensifying the ethanol taste.

Similarly, the use of the mixtures according to the invention for intensifying and/or for producing the impression of freshness, the menthol taste, peppermint taste or ethanol taste of cosmetic preparations, oral hygiene products, pharmaceutical preparations, foodstuffs and flavoring or perfume preparations is claimed.

Compounds of formula (I) or the mixtures according to the invention can in particular produce an ethanol taste in the absence of ethanol, and if ethanol is present they intensify the ethanol taste. Another aspect of the invention relates to the use of the compounds of formula (I) or the mixtures according to the invention for the production of ethanol-free or ethanol-reduced cosmetic preparations, oral hygiene products, pharmaceutical preparations, foodstuffs and flavoring or perfume preparations with an ethanol taste. Furthermore, the invention relates to cosmetic preparations, oral hygiene products, pharmaceutical preparations, foodstuffs and flavoring or perfume preparations with an ethanol content of about 0-40 wt %, preferably 0.5 to 30 wt % containing compounds of formula (I) or the mixtures according to the invention.

Finally the invention relates to medicinal products containing the mixtures according to the invention for clearing the respiratory passages.

EXAMPLES

Production Example H1

Production of 2-phenyl-but-2-enal 51 g of sodium acetate was dissolved in 100 g of water and 100 g of ethanol was added. At 15° C., 120 g of phenylacetaldehyde and 61.7 g of acetaldehyde were added in parallel within 1 hour. It was stirred firstly for 3.5 hours at room temperature and then for 13 hours under reflux. After adding 500 g of water, the phases were separated. The aqueous phase was extracted with methyl-tert.-butyl ether and the combined organic phases were washed with water. After distilling off the solvent, 137 g of raw product was obtained. This was distilled at a jacket temperature of 120° C. and a vacuum of 2 mbar in a thin-film evaporator, with 74 g of distillate being obtained. To separate unreacted phenylacetaldehyde, the distillate was submitted to further distillation on a 10-cm packed column. 65.5 g of material remained, which contained 94.3% of trans- and 3.4% of cis-product isomer.

Example 1

Panel Testing of Fondant Samples 11 subjects trained in tasting were asked to collect the descriptors required for describing the samples and to characterize them in their perception of intensity. The descriptors listed below in the net diagram (scale from 0 to 10) were tested.

A sample contained a standard fondant with a menthol content of 0.05 wt % without 2-phenyl-but-2-enal and the comparative sample contained 0.05 wt % of menthol and additionally 100 ppm of 2-phenyl-but-2-enal.

Accordingly, the compound according to the invention does not alter the desirable taste profile of the flavoring; in fact it intensifies the desirable taste impressions. The intensity of menthol, coolness and impact [initial flavor, initial impression of taste] is intensified and the overall action of the flavoring develops better (descriptors menthol, cooling and impact). The results of the sensory assessment are presented in Table 1.

TABLE 1

| Sensory assessment | | |
|---|---|---|
|  | Fondant with 0.05 wt % menthol | Fondant with 0.05 wt % menthol and 100 ppm 2-phenyl-but-2-enal |
| Cooling effect | 5.5 | 7.3 |
| Impact | 4.1 | 6.0 |
| Menthol | 5.8 | 7.8 |

Example 2

Flavor and Aroma Compositions and Formulation Examples

TABLE 2.1

Peppermint type flavor (data in wt %)

| Constituent | Proportion |
|---|---|
| 2-Phenyl-but-2-enal | 2 |
| Anethole | 9 |
| 1-Methol (natural or synthetic) | 35 |
| Peppermint oil *Piperita* type (natural or reconstituted) | 20 |
| Peppermint oil *Arvensis* type (natural or reconstituted) | 30 |
| TOTAL | 100 |

Example 2.2

| Peppermint type flavor Cool (data in wt %) | |
|---|---|
| Constituent | Proportion [%] |
| 2-Phenyl-but-2-enal | 4 |
| Anethole | 9 |
| 1-Methol (natural or synthetic) | 35 |
| Peppermint oil *Piperita* type (natural or reconstituted) | 20 |
| Peppermint oil *Arvensis* type (natural or reconstituted) | 20 |
| 2-Isopropyl-N,2,3-trimethylbutyramide (WS-23) | 2 |
| (1R,2S,5R)-N-Ethyl-2-isopropyl-5-methylcyclohexanecarboxamide (WS-3) | 2 |
| Menthol-propyleneglycol-carbonate (Frescolat MPC ®) | 2 |
| Menthol-ethyleneglycol-carbonate (Frescolat MGC ®) | 2 |
| l-Menthyl lactate (Frescolat ML ®) | 2 |
| TOTAL | 100 |

Example 2.3

| Spearmint type flavor (data in wt %) | |
|---|---|
| Constituent | Proportion [%] |
| 2-Phenyl-but-2-enal | 1 |
| Anethole | 9 |
| 1-Methol (natural or synthetic) | 30 |
| Peppermint oil *Piperita* type (natural or reconstituted) | 5 |
| Peppermint oil *Arvensis* type (natural or reconstituted) | 5 |
| l-Carvone | 15 |
| Spearmint oil *Cardiaca* type (natural or reconstituted) | 15 |
| Spearmint oil *Spicata* type (natural or reconstituted) | 15 |
| TOTAL | 100 |

Example 2.4

| Wintergreen type flavor (data in wt %) | |
|---|---|
| Constituent | Proportion [%] |
| 2-Phenyl-but-2-enal | 3 |
| Anethole | 9 |
| 1-Methol (natural or synthetic) | 45 |
| Peppermint oil *Piperita* type (natural or reconstituted) | 2 |
| Peppermint oil *Arvensis* type (natural or reconstituted) | 3 |
| Spearmint oil *Spicata* type (natural or reconstituted) | 1 |
| Eugenol | 7 |
| Eucalyptol | 5 |
| Methylsalicylate | 20 |
| TOTAL | 100 |

Example 2.5

| Wintergreen type flavor Cool | |
|---|---|
| Constituent | Proportion [%] |
| 2-Phenyl-but-2-enal | 5 |
| Anethole | 9 |
| 1-Methol (natural or synthetic) | 40 |
| Peppermint oil *Piperita* type (natural or reconstituted) | 2 |
| Peppermint oil *Arvensis* type (natural or reconstituted) | 3 |
| Spearmint oil *Spicata* type (natural or reconstituted) | 1 |
| Eugenol | 7 |
| Eucalyptol | 5 |
| Methylsalicylate | 16 |
| 2-Isopropyl-N,2,3-trimethylbutyramide (WS-23) | 2 |
| (1R,2S,5R)-N-Ethyl-2-isopropyl-5-methylcyclohexanecarboxamide (WS-3) | 2 |
| Menthol-propyleneglycol-carbonate (Frescolat MPC ®) | 2 |
| Menthol-ethyleneglycol-carbonate (Frescolat MGC ®) | 2 |
| l-Menthyl lactate (Frescolat ML ®) | 2 |
| (1R,2S,5R)-N-(4-Methoxyphenyl)-2-isopropyl-5-methylcyclohexanecarboxamide (WS-12) | 1 |
| TOTAL | 100 |

Example 2.6

| *Eucalyptus* type flavor (data in wt %) | |
|---|---|
| Constituent | Proportion [%] |
| 2-Phenyl-but-2-enal | 2 |
| Anethole | 18 |
| Eucalyptol | 15 |
| Eucalyptus oil | 5 |
| 1-Methol (natural or synthetic) | 50 |
| Peppermint oil *Piperita* type (natural or reconstituted) | 2 |
| Peppermint oil *Arvensis* type (natural or reconstituted) | 3 |
| TOTAL | 100 |

Example 2.7

| Eucalyptus type flavor Cool (data in wt %) | |
|---|---|
| Constituent | Proportion [%] |
| 2-Phenyl-but-2-enal | 4 |
| Mentholmethyl ether | 4 |
| Anethole | 18 |
| Eucalyptol | 15 |
| Eucalyptus oil | 5 |
| 1-Methol (natural or synthetic) | 44 |
| Peppermint oil *Piperita* type (natural or reconstituted) | 2 |
| Peppermint oil *Arvensis* type (natural or reconstituted) | 3 |
| Menthoneglycerol acetal (Frescolat MGA ®) | 5 |
| TOTAL | 100 |

Example 2.8

| Cinnamon type flavor (data in wt %) | |
|---|---|
| Constituent | Proportion [%] |
| 2-Phenyl-but-2-enal | 0.5 |
| Cinnamaldehyde | 10 |
| Anethole | 9 |
| Eugenol | 2 |
| 1-Methol (natural or synthetic) | 40 |
| Peppermint oil Piperita type (natural or reconstituted) | 10 |
| Peppermint oil Arvensis type (natural or reconstituted) | 15 |
| Spearmint oil Spicata type (natural or reconstituted) | 8 |
| TOTAL | 100 |

Example 2.9

| Cinnamon type flavor Cool (data in wt %) | |
|---|---|
| Constituent | Proportion [%] |
| 2-Phenyl-but-2-enal | 2 |
| Menthylmethyl ether | 3 |
| Cinnamaldehyde | 10 |
| Anethole | 9 |
| Eugenol | 2 |
| 1-Methol (natural or synthetic) | 40 |
| Peppermint oil Piperita type (natural or reconstituted) | 10 |
| Peppermint oil Arvensis type (natural or reconstituted) | 10 |
| Spearmint oil Spicata type (natural or reconstituted) | 8 |
| (1R,2S,5R)-N-Ethyl-2-isopropyl-5-methylcyclohexanecarboxamide (WS-3) | 2 |
| (1R,2S,5R)-N-[4-(Cyanomethyl)phenyl]-2-isopropyl-5-methylcyclohexanecarboxamide | 0.5 |
| (1R,2S,5R)-N-[2-(Pyridin-2-yl)-ethyl]-2-isopropyl-5-methylcyclohexanecarboxamide | 0.5 |
| Menthoneglycerol acetal (Frescolat MGA ®) | 1 |
| Menthol-propyleneglycol-carbonate (Frescolat MPC ®) | 1 |
| TOTAL | 100 |

These aroma compositions are as a rule incorporated in the following concentrations in corresponding embodiment examples:

Toothpaste: 0.8-1.5 wt %

Mouthwash: 0.1-0.25 wt %

Mouthwash concentrate: 1-4 wt %

Chewing gum: 1-2 wt %

Candies: 0.1-0.3 wt %

Embodiment Examples for the Aforementioned Flavor Compositions

Example 2.10

| Sugar-free chewing gum with Cinnamon type flavor Cool (data in wt %) | |
|---|---|
| Constituent | Proportion |
| Gum base | 30.00 |
| Sorbitol, powdered | 40.00 |
| Isomalt, powdered | 9.50 |
| Xylitol | 2.00 |
| Mannitol D | 3.00 |
| Aspartame | 0.10 |
| Acesulfame K | 0.10 |
| Emulgum/Plasticizing agent | 0.30 |
| Sorbitol (70% in water) | 13.00 |
| Glycerol | 1.00 |
| Flavor cinnamon type Cool | 1.00 |
| TOTAL | 100 |

At a dosage of 1% of the aroma composition in the chewing gum, 2-phenyl-but-2-enal produces a definite "boost effect" and imparts—compared to the flavor not according to the invention—an intensified feeling of freshness together with an increased menthol taste and perception of coolness, especially in the initial phase of consumption.

Example 2.11

| Standard chewing gum with peppermint type flavor (data in wt %) | |
|---|---|
| Constituent | Proportion [%] |
| Gum base | 21.00 |
| Glucose syrup | 16.50 |
| Glycerol | 0.50 |
| Sugar, powdered | 60.00 |
| Peppermint type flavor | 2.00 |
| TOTAL | 100 |

At a dosage of 2% of the aroma composition in the chewing gum, 2-phenyl-but-2-enal produces an intensified feeling of freshness together with an increased menthol taste and perception of coolness and imparts—compared to the flavor not according to the invention—greater palatefulness, especially at the start of chewing.

Example 2.12

| Toothpaste (phosphate base) with spearmint type flavor (data in wt %) | |
|---|---|
| Constituent | Proportion |
| Deionized water | 36.39 |
| Glycerol | 20.00 |
| Solbrol M (sodium salt) | 0.15 |
| Sodium monofluorophosphate | 0.76 |
| Saccharin | 0.20 |
| Dicalcium phosphate dihydrate | 36.00 |
| Aerosil 200 | 3.00 |
| Sodium carboxymethylcellulose | 1.20 |
| Sodium lauryl sulfate (Texapon) | 1.30 |
| Spearmint type flavor | 1.00 |
| TOTAL | 100 |

At a dosage of 1% of the aroma composition in the toothpaste, on brushing, 2-phenyl-but-2-enal produces an intensification of the effect of the flavor and imparts—compared to the flavor not according to the invention—a definite feeling of freshness together with an increased menthol taste and perception of coolness, especially at the start of brushing.

Example 2.13

| Toothpaste (transparent gel formulation) with cinnamon type flavor (data in wt %) | |
|---|---|
| Constituent | Proportion |
| Sorbitol 70% | 63.00 |
| Deionized water | 11.31 |
| Saccharin | 0.20 |
| Sodium monofluorophosphate | 1.14 |
| Solbrol | 0.15 |
| Trisodium phosphate | 0.10 |
| PEG 1500 (PEG 32) | 5.00 |
| Sident 9 (Abrasive Silica) | 8.00 |
| Sident 22 S (Thickening Silica) | 8.00 |
| Sodium carboxymethylcellulose | 0.60 |
| Sodium lauryl sulfate | 1.50 |
| Cinnamon type flavor | 1.00 |
| TOTAL | 100 |

At a dosage of 1% of the aroma composition in the toothpaste, owing to the 2-phenyl-but-2-enal, on brushing the paste acquires a clearer freshness profile together with an increased menthol taste and perception of coolness and imparts—compared to the flavor not according to the invention—a definite retronasal cooling.

Example 2.14

| Toothpaste ("Silica opaque") with peppermint type flavor Cool (data in wt %) | |
|---|---|
| Constituent | Proportion |
| Deionized water | 26.53 |
| Sorbitol 70% | 45.00 |
| Solbrol M Na-salt | 0.15 |
| Trisodium phosphate | 0.10 |
| Saccharin | 0.20 |
| Sodium monofluorophosphate | 1.12 |
| PEG 1500 | 5.00 |
| Sident 9 (Abrasive Silica) | 10.00 |
| Sident 22 S (Thickening Silica) | 8.00 |
| Sodium carboxymethylcellulose | 0.90 |
| Titanium (IV) oxide | 0.50 |
| Sodium lauryl sulfate (SLS) | 1.50 |
| Peppermint type flavor Cool | 1.00 |
| TOTAL | 100 |

At a dosage of 1% of the aroma composition in the toothpaste, owing to the 2-phenyl-but-2-enal, on brushing, the paste has enhanced palatefulness and achieves—compared to the flavor not according to the invention—a fresher mouthfeel together with an increased menthol taste and perception of coolness.

Example 2.15

| Toothpaste (calcium carbonate base) with eucalyptus type flavor Cool (data in wt %) | |
|---|---|
| Constituent | Proportion |
| Deionized water | 27.50 |
| Saccharin | 0.20 |
| Solbrol M Sodium salt | 0.20 |
| Sodium monofluorophosphate | 0.80 |
| Sorbitol 70% | 29.00 |
| Calcium carbonate | 35.00 |
| Sident 22 S (Thickening Silica) | 2.50 |
| Sodium carboxymethylcellulose | 1.30 |
| Titanium (IV) oxide | 0.50 |
| Sodium lauryl sulfate | 2.00 |
| Eucalyptus type flavor Cool | 1.00 |
| TOTAL | 100 |

At a dosage of 1% of the aroma composition in this toothpaste, there is marked improvement—compared to the flavor not according to the invention—of the sensory profile and the total impression is convincing through increased freshness together with an increased menthol taste and perception of coolness.

Example 2.16

| Mouthwash concentrate with wintergreen type flavor (data in wt %) | |
|---|---|
| Constituent | Proportion |
| Ethyl alcohol 96% | 42.00 |
| Cremophor RH 455 | 5.00 |
| Deionized water | 48.67 |
| Allantoin | 0.20 |
| Sodium saccharin 450 | 0.10 |
| Color L-Blue 5000 (1% in water) | 0.03 |
| Wintergreen type flavor | 4.00 |
| TOTAL | 100 |

At a dosage of 4% of the aroma composition in this mouthwash, there is convincing improvement—compared to the flavor not according to the invention—of the taste through stronger and quicker cooling in the oral cavity.

Example 2.17

Mouthwash ("ready to use" without alcohol) with eucalyptol type flavor (data in wt %)

| Constituent | Proportion |
| --- | --- |
| Cremophor RH 455 | 1.80 |
| Deionized water | 87.57 |
| Sorbitol 70% | 10.00 |
| Sodium fluoride | 0.18 |
| Sodium saccharin 450 | 0.10 |
| Solbrol M Sodium salt | 0.15 |
| Eucalyptol type flavor | 0.2 |
| TOTAL | 100 |

Example 2.18

Mouthwash ("ready to use" with alcohol) with wintergreen type flavor Cool (data in wt %)

| Constituent | Proportion |
| --- | --- |
| Ethyl alcohol 96% | 10.00 |
| Cremophor CO 40 | 1.00 |
| Benzoic acid | 0.12 |
| Deionized water | 83.46 |
| Sorbitol 70% | 5.00 |
| Sodium saccharin 450 | 0.07 |
| L-Blue 5000 (1% in water) | 0.10 |
| Wintergreen type flavor Cool | 0.25 |
| TOTAL | 100 |

Example 2.19

Candy ("Hardboiled candy"), sugar-free with peppermint type flavor (data in wt %)

| Constituent | Proportion |
| --- | --- |
| Water | 2.24 |
| Isomalt | 94.98 |
| Xylitol | 2.40 |
| Sucralose | 0.03 |
| Acesulfame K | 0.050 |
| Citric acid | 0.050 |
| Peppermint type flavor | 0.25 |
| TOTAL | 100 |

Example 2.20

Candy ("Hardboiled candy") with spearmint type flavor (data in wt %)

| Constituent | Proportion |
| --- | --- |
| Water | 2.75 |
| Sugar | 60.1 |
| Glucose syrup | 36.9 |
| Spearmint type flavor | 0.25 |
| TOTAL | 100 |

Example 2.21

Sugar-free chewing gum (data in wt %)

| Ingredients | Amount |
| --- | --- |
| Chewing gum base | 30.00 |
| Sorbitol, powdered | Ad 100 |
| Palatinit | 9.50 |
| Xylitol | 2.00 |
| Mannitol | 3.00 |
| Aspartame | 0.10 |
| Acesulfame K | 0.10 |
| Emulsifier | 0.30 |
| Sorbitol 70% in water | 14.00 |
| Glycerol | 1.00 |
| Wintergreen type flavor Cool | 1.80 |
| TOTAL | 100 |

Example 3

Mouthwash

| Constituent | 3a) | 3b) | 3c) | 3d) |
| --- | --- | --- | --- | --- |
| Ethanol 96% | 42.00 | 42.00 | 30.00 | 30.00 |
| Cremophor RH 455 | 5.00 | 5.00 | 5.00 | 5.00 |
| Deionized water | 51.67 | 51.67 | 63.67 | 63.67 |
| Allantoin | 0.20 | 0.20 | 0.20 | 0.20 |
| Sodium saccharin 450 | 0.10 | 0.10 | 0.10 | 0.10 |
| Color L-Blue 5000 (1% in water) | 0.03 | 0.03 | 0.03 | 0.03 |
| Peppermint type flavor from example 2.2 with or without 2-phenyl-but-2-enal (the missing proportion in recipes 3a and c was replaced with water) | 1.00 (not containing 2-phenyl-but-2-enal) | 1.00 (containing 2-phenyl-but-2-enal) | 1.00 (containing 2-phenyl-but-2-enal) | 1.00 (not containing 2-phenyl-but-2-enal) |
| TOTAL | 100 | 100 | 100 | 100 |
| Intensity of the ethanol taste | 4.9 | 7.6 | 5.2 | 3.1 |

A trained panel assessed the intensity of the ethanol taste on a scale from 1 to 10 (0=no ethanol taste, 10=very strong ethanol taste). Example 3b shows that addition of 2-phenyl-but-2-enal to example 3a produces a definite increase in intensity of the ethanol taste. Example 3c shows that addition of 2-phenyl-but-2-enal with simultaneous decrease in the proportion of ethanol has the effect that even so, an almost comparable level of ethanol intensity is perceived as in example 3a.

The invention claimed is:

1. A flavor composition having an improved cooling sensation, the flavor or aroma composition comprising:
a physiological cooling agent to provide a cooling sensation; and
an effective amount of a phenylalkenal of formula (I)

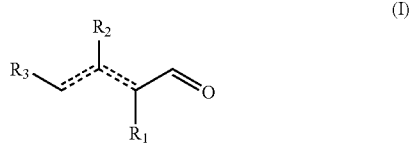

to intensify the cooling sensation;
wherein $R_1$ and $R_2$ independently of one another represent hydrogen, a methyl or phenyl residue, $R_3$ stands for hydrogen, a phenyl, an alkenyl or a linear or branched alkyl residue with 1 to 5 carbon atoms, and the broken double lines represent, independently of one another, a single bond or a double bond.

2. The flavor composition of claim 1, wherein $R_1$ and $R_2$ are different and denote hydrogen or phenyl, $R_3$ stands for hydrogen, an alkenyl or a linear or branched alkyl group with 1 to 5 carbon atoms, and the broken double lines represent, independently of one another, a single bond or a double bond.

3. The flavor composition of claim 1, wherein the phenylalkenal of formula (I) is selected from a group comprising 2-phenyl-but-2-enal, 3-phenyl-pent-4-enal, 2-phenyl-pent-4-enal and mixtures thereof.

4. The flavor composition of claim 1, wherein the phenylalkenal of formula (I) is mixture of 2-phenyl-pent-2-enal and a phenylalkenal selected from a group comprising 2-phenyl-but-2-enal, 3-phenyl-pent-4-enal, 2-phenyl-pent-4-enal, and mixtures thereof.

5. The flavor composition of claim 1, wherein the effective amount of the phenylalkenal of formula (I) ranges from about 1 weight percent to about 99 weight percent of the flavor composition.

6. The flavor composition of claim 1, wherein the effective amount of the phenylalkenal of formula (I) ranges from about 1 weight percent to about 80 weight percent of the flavor composition.

7. The flavor composition of claim 1 wherein the effective amount of the phenylalkenal of formula (I) ranges from about 1 weight percent to about 70 weight percent of the flavor composition.

8. A cosmetic preparation containing the flavor composition as claimed in claim 1.

9. An oral hygiene products containing the flavor composition as claimed in claim 1.

10. A pharmaceutical preparation containing the flavor composition as claimed in claim 1.

11. A foodstuff containing the flavor composition as claimed in claim 1.

12. A flavoring or perfume preparation containing the flavor composition as claimed in claim 1.

13. The flavor composition of claim 1, wherein the effective amount of the phenylalkenal of formula (I) ranges from about 1 weight percent to about 30 weight percent of the flavor composition.

14. The flavor composition of claim 1, wherein the effective amount of the phenylalkenal of formula (I) ranges from about 1 weight percent to about 20 weight percent of the flavor composition.

15. The flavor composition of claim 1, wherein the effective amount of the phenylalkenal of formula (I) ranges from about 1 weight percent to about 5 weight percent of the flavor composition.

16. The flavor composition of claim 1, wherein the effective amount of the phenylalkenal of formula (I) ranges from about 20 weight percent to about 80 weight percent of the flavor composition.

17. The flavor composition of claim 1, wherein the effective amount of the phenylalkenal of formula (I) ranges from about 20 weight percent to about 70 weight percent of the flavor composition.

18. The flavor composition of claim 1, wherein the effective amount of the phenylalkenal of formula (I) ranges from about 30 weight percent to about 70 weight percent of the flavor composition.

19. A flavor composition having an improved cooling sensation, the flavor composition consisting essentially of:
a physiological cooling agent to provide a cooling sensation;
an effective amount of a phenylalkenal of formula (I)

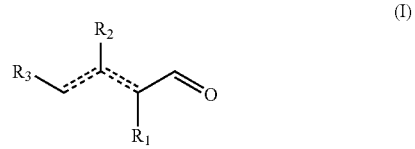

to intensify the cooling sensation,
where $R_1$ and $R_2$ independently of one another represent hydrogen, a methyl or phenyl residue, $R_3$ stands for hydrogen, a phenyl, an alkenyl or a linear or branched alkyl residue with 1 to 5 carbon atoms, and the broken double lines represent, independently of one another, a single bond or a double bond; and
an aroma substance.

20. A flavor composition having an improved cooling sensation, the flavor composition consisting essentially of:
a physiological cooling agent to provide a cooling sensation; and
an effective amount of a phenylalkenal of formula (I)

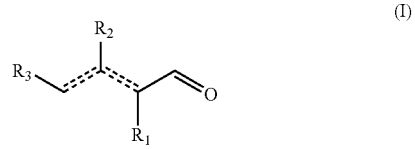

to intensify the cooling sensation;
wherein $R_1$ and $R_2$ independently of one another represent hydrogen, a methyl or phenyl residue, $R_3$ stands for hydrogen, a phenyl, an alkenyl or a linear or branched alkyl residue with 1 to 5 carbon atoms, and the broken double lines represent, independently of one another, a single bond or a double bond.

* * * * *